(12) United States Patent
Arcenio et al.

(10) Patent No.: US 8,142,463 B2
(45) Date of Patent: Mar. 27, 2012

(54) BATTERY OPERATED NUCLEUS DISRUPTOR DEVICE FOR INTERVERTEBRAL DISC

(75) Inventors: Greg Arcenio, Redwood City, CA (US); Lex P. Jansen, Pleasanton, CA (US)

(73) Assignee: Kyphon Sarl, Neuchatel (CH)

( * ) Notice: Subject to any disclaimer, the term of this patent is extended or adjusted under 35 U.S.C. 154(b) by 354 days.

(21) Appl. No.: 12/403,598

(22) Filed: Mar. 13, 2009

(65) Prior Publication Data

US 2010/0234866 A1   Sep. 16, 2010

(51) Int. Cl.
*A61B 17/32* (2006.01)
(52) U.S. Cl. ...................................... 606/170
(58) Field of Classification Search .......... 600/564–568; 604/22; 606/79, 80, 82–84, 125, 159, 167, 606/170, 171, 176, 179, 180, 185
See application file for complete search history.

(56) References Cited

U.S. PATENT DOCUMENTS

| | | | | |
|---|---|---|---|---|
| 4,306,570 A | * | 12/1981 | Matthews | 600/567 |
| 4,883,458 A | * | 11/1989 | Shiber | 604/22 |
| 2006/0206128 A1 | * | 9/2006 | Conquergood et al. | 606/180 |
| 2007/0068329 A1 | * | 3/2007 | Phan et al. | 74/543 |

* cited by examiner

*Primary Examiner* — Ryan Severson

(57) ABSTRACT

Apparatuses and methods for accessing and disrupting a tissue are disclosed herein. In one embodiment, an apparatus includes a first elongate member having a tissue interaction portion disposed at a distal end of the first elongate member. The tissue interaction portion is configured to be inserted within a biological body. A second elongate member is movably disposed within a lumen defined by the first elongate member. The second elongate member has a threaded exterior surface. A drive motor is coupled to the first elongate member and coupled to the second elongate member. The drive motor is configured to rotate the first elongate member in a first direction and configured to rotate the second elongate member in a second direction opposite the first direction. The tissue interaction portion is configured to disrupt tissue when disposed into the biological body and when the first elongate member is rotated.

18 Claims, 21 Drawing Sheets

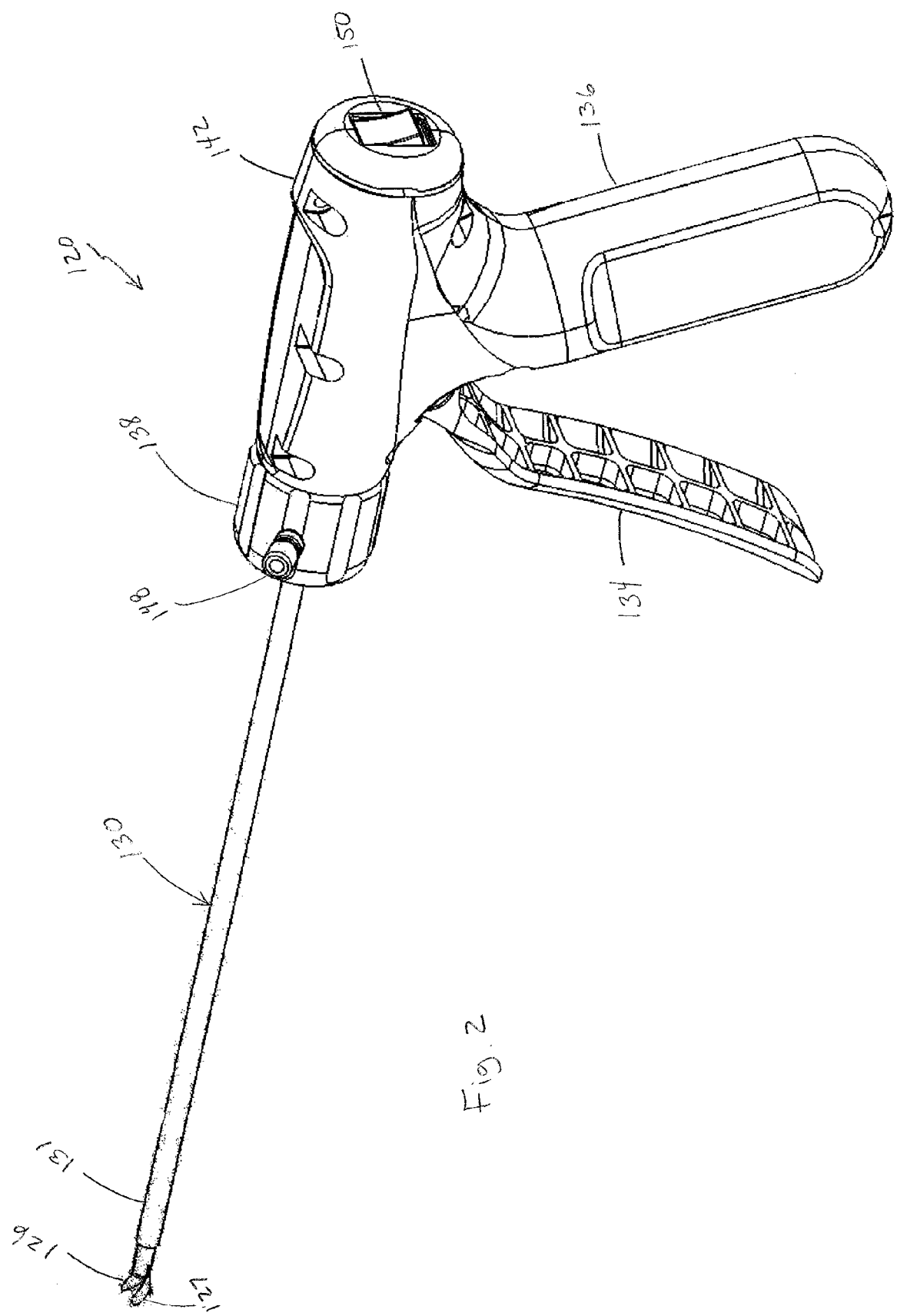

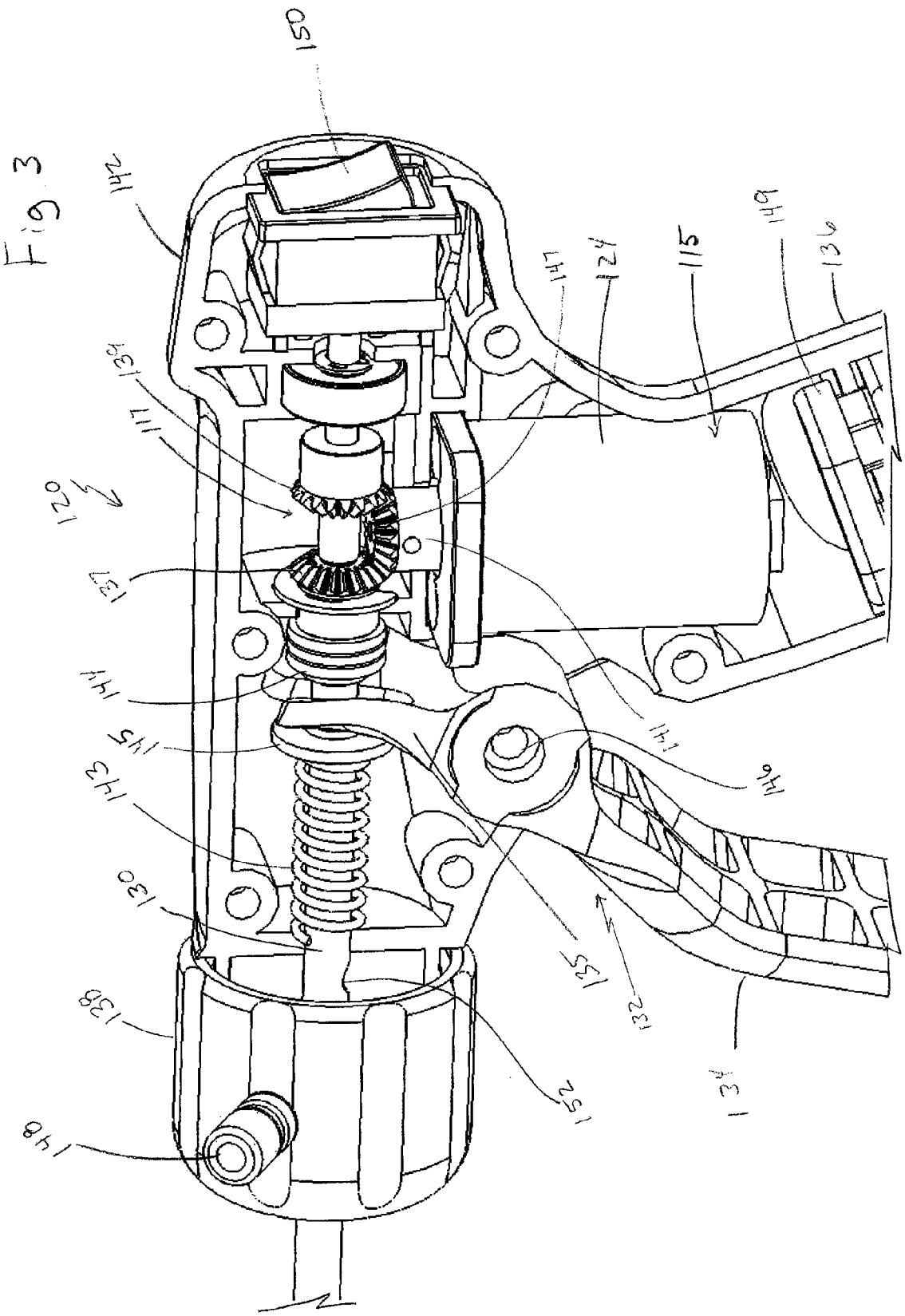

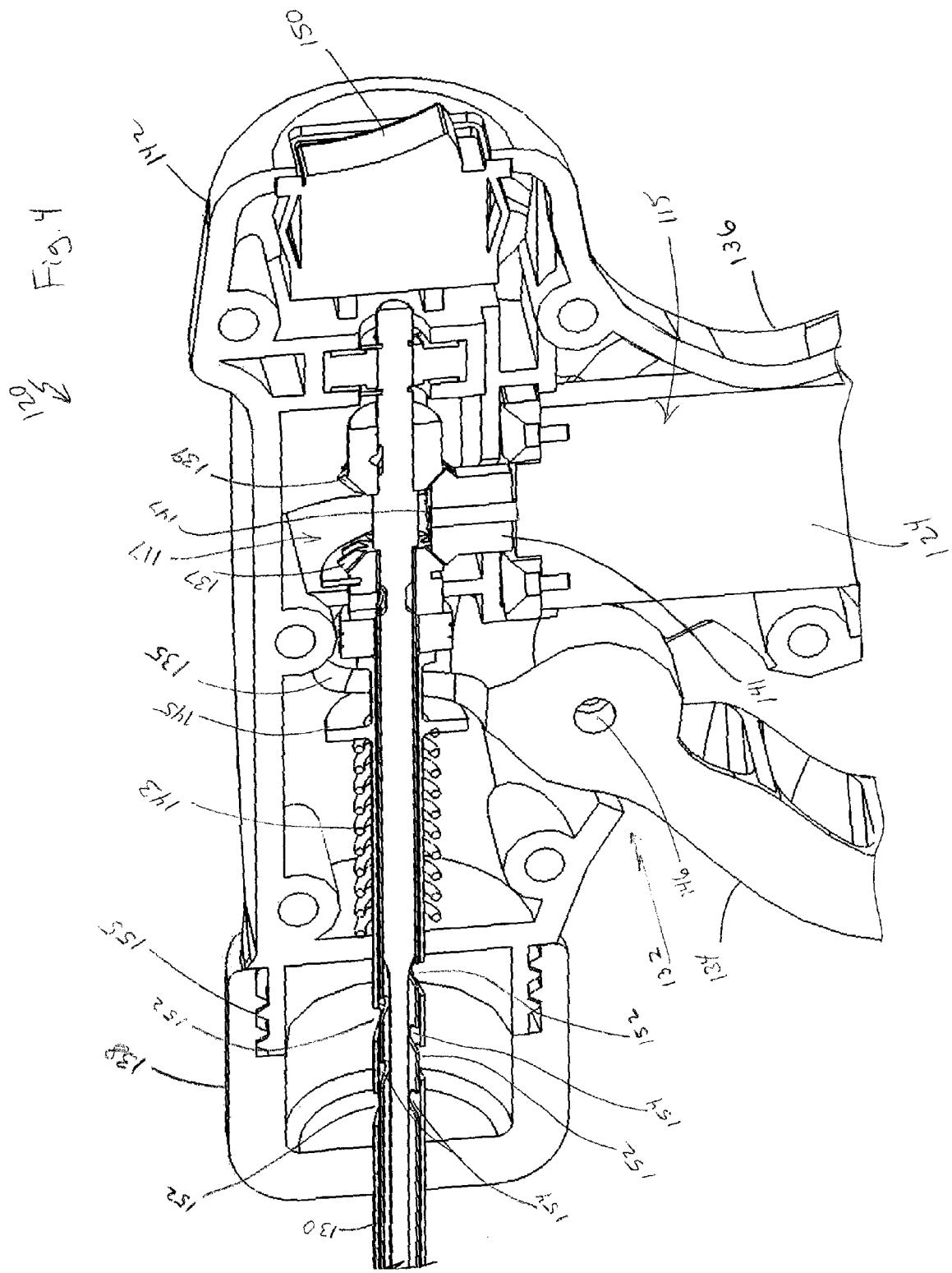

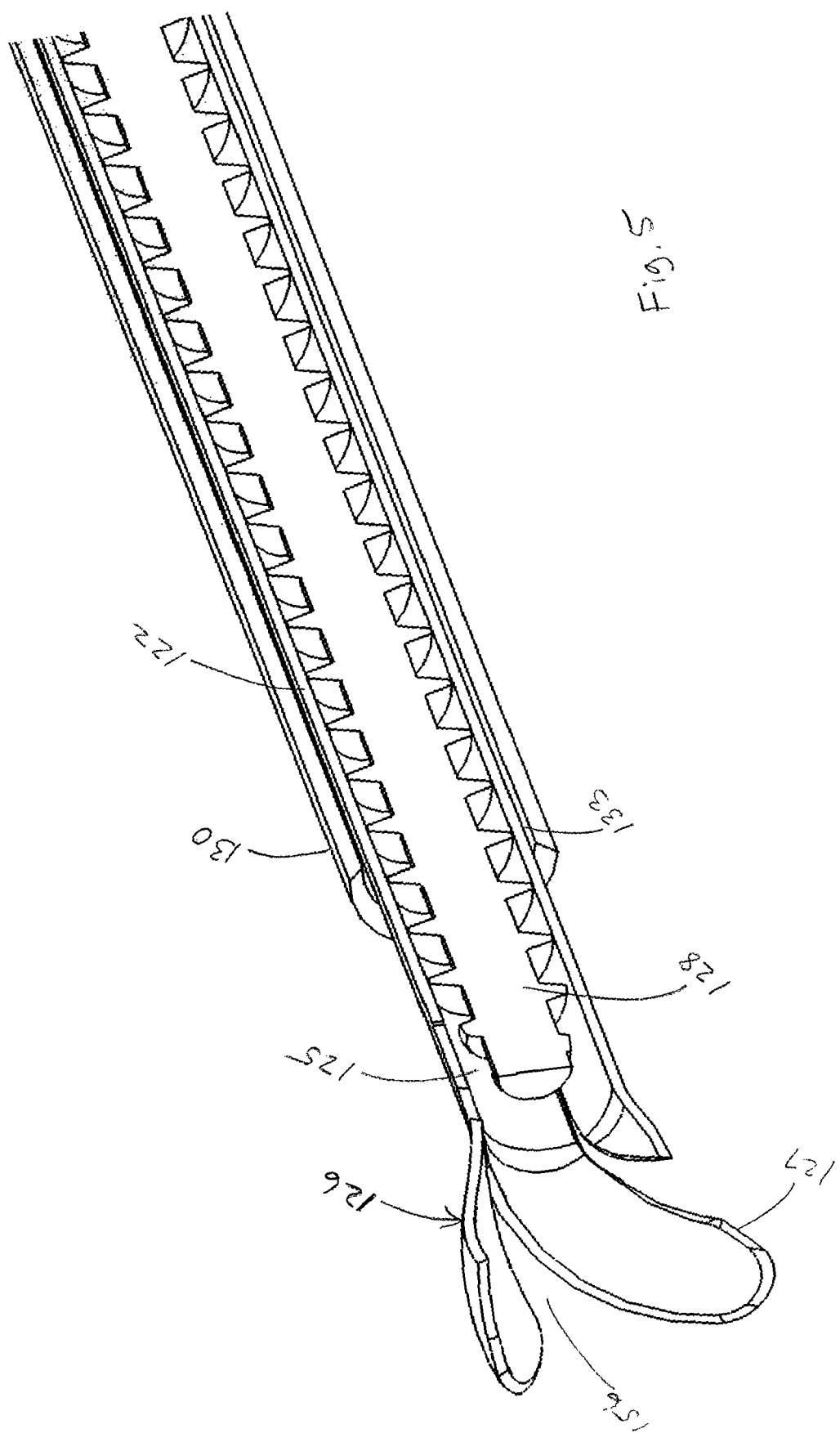

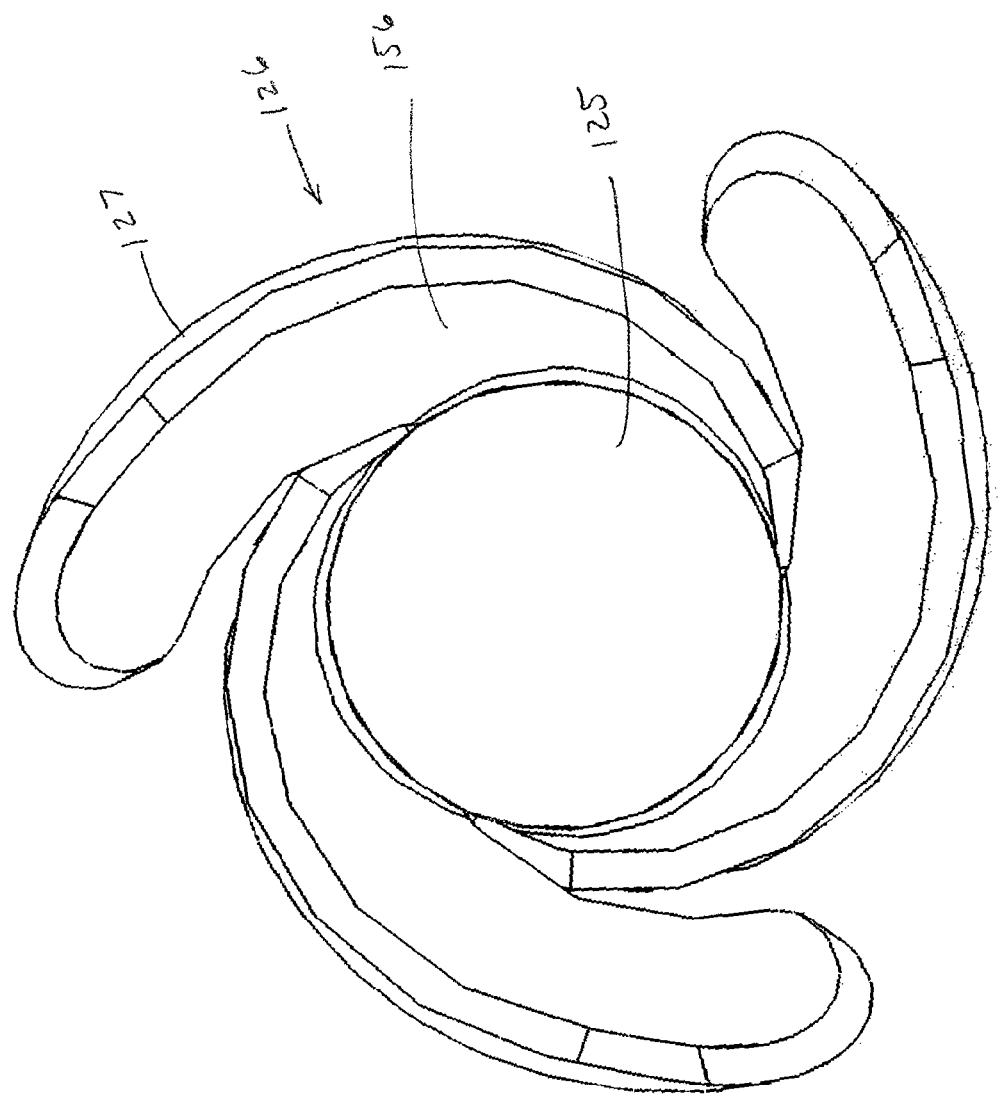

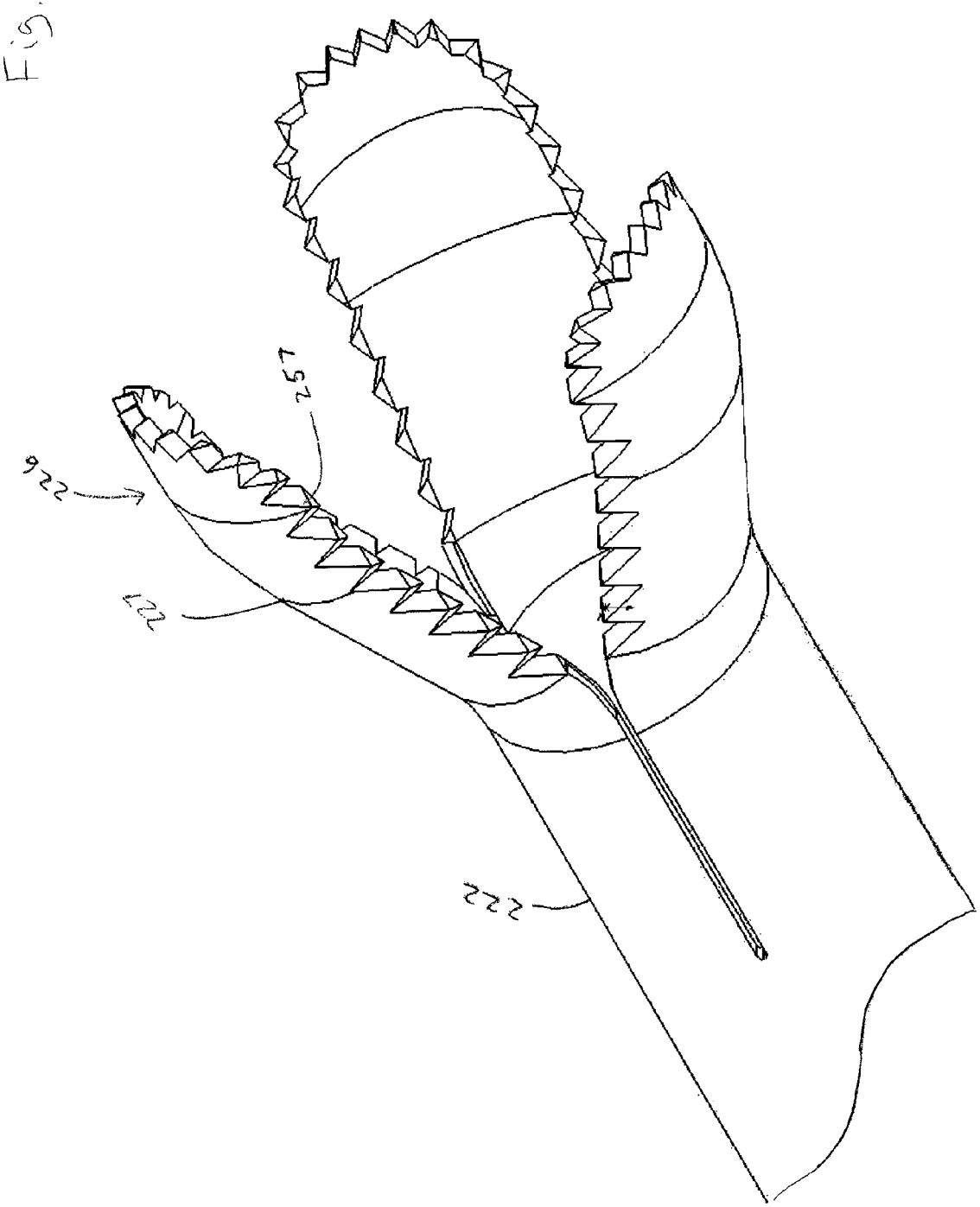

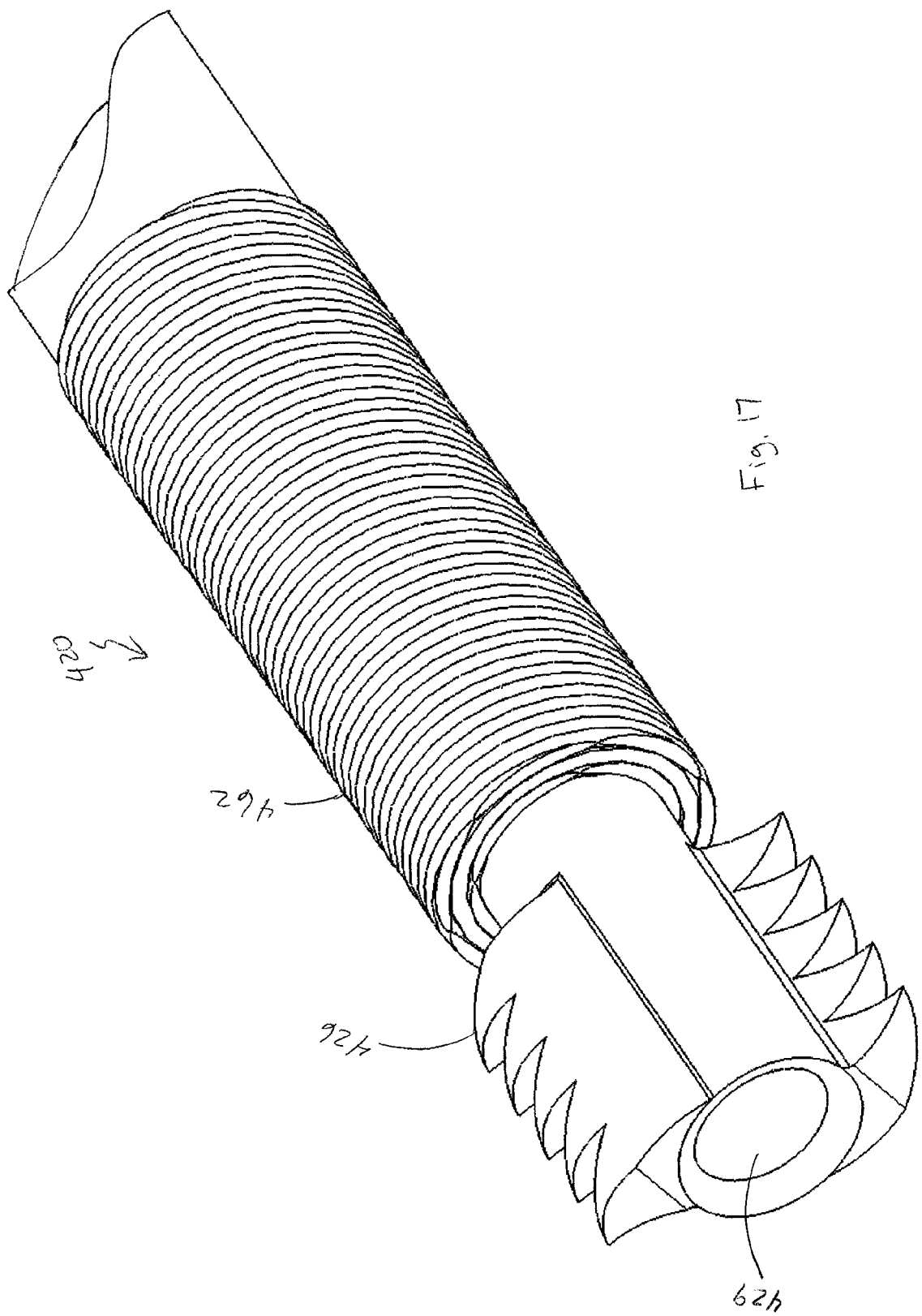

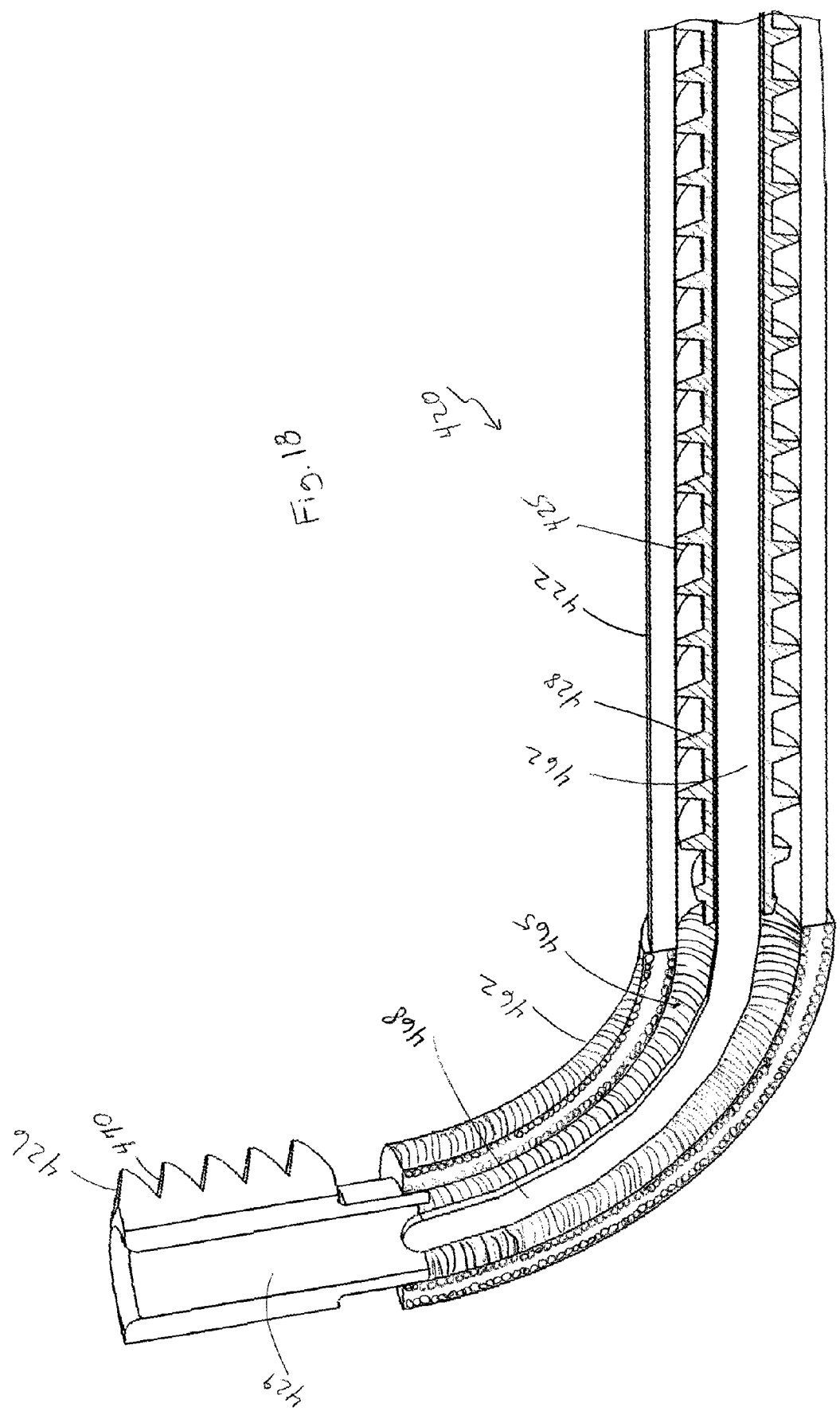

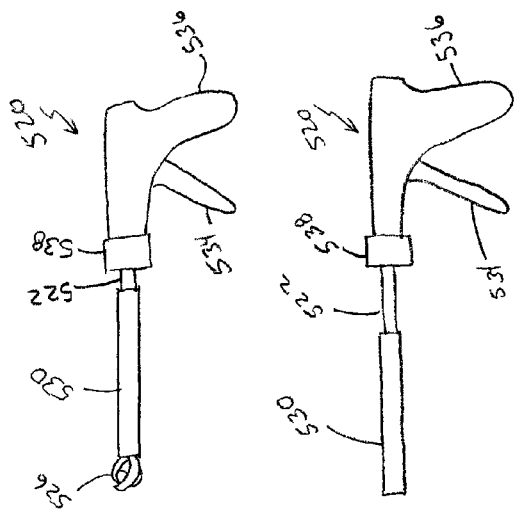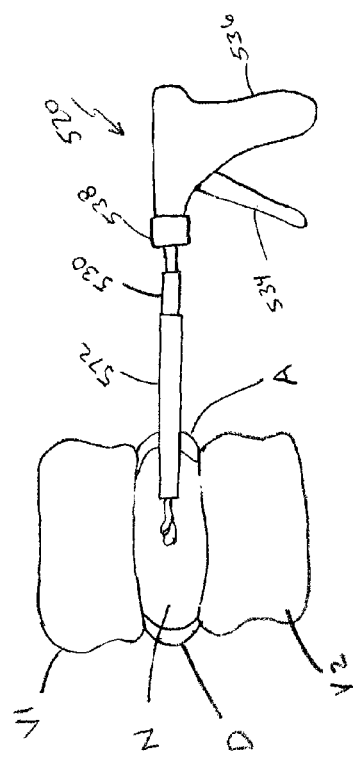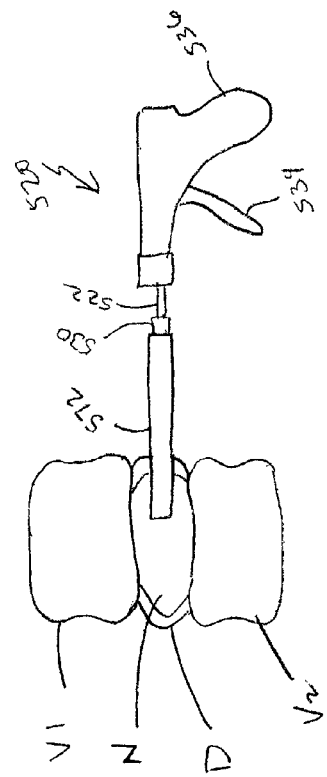

BATTERY OPERATED NUCLEUS DISRUPTOR DEVICE FOR INTERVERTEBRAL DISC

BACKGROUND

The invention relates generally to medical devices and procedures, including, for example, a medical device for percutaneously accessing a biological body, and disrupting tissue within the biological body.

Known medical devices are configured to access percutaneously a vertebra, an intervertebral disc, or other areas of a spine to perform a variety of different medical procedures. Some known medical devices are configured to remove tissue from within the interior of a vertebra or intervertebral disc. Other known medical devices are configured to provide cutting means to tear, disrupt and/or loosen tissue within a vertebra or intervertebral disc.

In some medical procedures, a medical device used for disrupting tissue can be difficult to maneuver with the biological body. For example, it may be desirable to rotate a device while it is disposed within a biological body. Such rotation, however, may be difficult for the physician to perform. For example, it may be difficult for a physician to repeatedly twist his/her arm to rotate the medical device within a biological body. In addition, in some medical procedures the device used to disrupt tissue may need to be repeatedly removed from the biological body and reinserted potentially damaging the integrity of the biological body.

Thus, a need exists for an apparatus and method for disrupting tissue, such as tissue within an intervertebral disc or a vertebra, where the apparatus can be expanded and collapsed, and/or rotated and/or maneuvered within the intervertebral disc or vertebra without repeated insertion and removal of the apparatus.

SUMMARY OF THE INVENTION

Devices and methods for accessing and disrupting a tissue are disclosed herein. In one embodiment, an apparatus includes a first elongate member having a tissue interaction portion disposed at a distal end of the first elongate member. The tissue interaction portion is configured to be inserted within a biological body. A second elongate member is movably disposed within a lumen defined by the first elongate member. The second elongate member has a threaded exterior surface. A drive motor is coupled to the first elongate member and coupled to the second elongate member. The drive motor is configured to rotate the first elongate member in a first direction and configured to rotate the second elongate member in a second direction opposite the first direction. The tissue interaction portion is configured to disrupt tissue when disposed into the biological body and when the first elongate member is rotated.

BRIEF DESCRIPTION OF THE DRAWINGS

FIG. 2 is a side perspective view of a medical device according to another embodiment.

FIG. 3 is a side perspective view of a portion of the medical device of FIG. 2 shown with a portion of the housing removed.

FIG. 4 is a cross-sectional view of a portion of the medical device of FIG. 2.

FIG. 5 is a cross-sectional side perspective view of a distal end portion of the medical device of FIG. 2, shown with the tissue interaction member in an expanded configuration.

FIG. 6 is a side view of a distal end portion of the medical device of FIG. 2 shown partially in cross-section and showing the tissue interaction member in a collapsed configuration.

FIG. 10 is a side perspective view of another embodiment of a tissue interaction member.

FIG. 17 is a side perspective view of a distal end portion of another embodiment of a medical device. shown in a first configuration.

FIG. 18 is a side cross-sectional view of a distal end portion of the medical device of FIG. 17 shown in a second configuration.

FIG. 19 is a side view of an embodiment of a medical device shown in a first configuration.

FIG. 20 is a side view of the medical device of FIG. 19 shown in a second configuration.

FIG. 21 is a side view of the medical device of FIG. 19 shown partially disposed within an access cannula within an intervertebral disc.

FIG. 22 is a side view of the medical device of FIG. 19 shown partially disposed within an access cannula and within an intervertebral disc.

DETAILED DESCRIPTION

Figure 1:
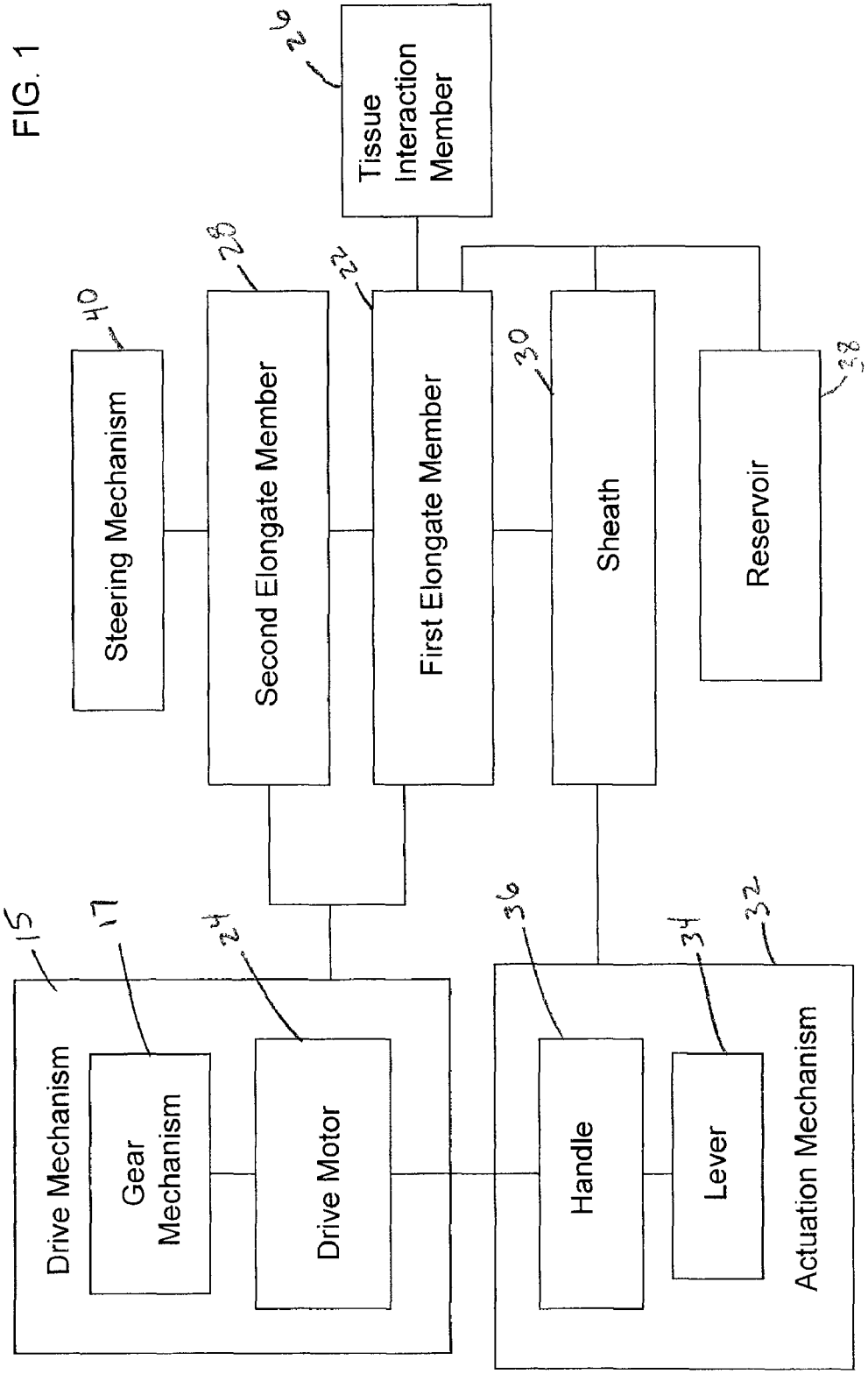
FIG. 1 is a schematic illustration of a medical device according to an embodiment.

The devices and methods described herein are configured for deployment within an interior area of a patient's body, such as within a hard tissue area (e.g., vertebra, bone structure) or soft tissue area of a patient (e.g., intervertebral disc). For example, the devices can be percutaneously inserted within a biological body of a patient. In some embodiments, a device described herein is used to disrupt, sever, and/or cut a portion of a tissue within a biological body, such as a vertebra or intervertebral disc. For example, a medical device can include a tissue interaction member that can be rotated while disposed within an interior area of a patient's body, or otherwise maneuvered such that a cutting portion of the tissue interaction member disrupts or cuts tissue within the interior area of the patient.

In some embodiments, a medical device as described herein can be used to cut, tear, disrupt, cleave or scrape biological material within a biological body to form a cavity to allow a user to more easily insert an inflation balloon tamp (IBT) and reduce the likelihood of ruptures to the balloon during inflation. The medical devices described herein can include an expandable tissue interaction member at a distal end portion of the medical device. The expandable tissue interaction member can include one or more arms. The arms can be elastically-deformable. For example, the arms can be formed with, for example, a nitinol material or superelastic nitinol material such that they can be shape-set into a biased expanded configuration. The arms of the expandable member can be actuated between a collapsed configuration for insertion into a biological body, and an expanded configuration for use in distracting, disrupting, scraping, tearing, and/or performing other operations on biological tissue within the biological body. The arms in the expanded configuration can, for example, have unconstrained ends (i.e., the distal tips of the arms are not attached to anything) and/or can each have a flared shape as described in more detail below.

The arms can be actuated, for example, using a sheath coupled to the expandable member. For example, the expandable member can be disposable within a lumen of the sheath. The sheath can be actuated to move between a first position in which the arms of the expandable member are disposed within the lumen of the sheath, and a second position in which the arms are disposed outside of the lumen of the sheath. In alternative embodiments, the sheath can be stationary and the expandable member can be moved relative to the sheath. For example, the expandable member can be moved between a first position in which the arms of the expandable member are disposed within the lumen of the sheath and a second position in which the arms are disposed outside of the lumen of the sheath.

A size (e.g., length, width, depth) of the arms and the quantity of the arms can be varied for use in different anatomical bodies, and to accommodate the formation of different sized cavities. For example, the size and/or pitch of the arms can be varied; the number and location of the arms can also be varied. In some embodiments, a medical device can have arms only on one side of the medical device. The medical device and arms can thus be sized or tailored for use in different medical procedures, and in different areas of anatomy.

In one embodiment, an apparatus includes a first elongate member having a tissue interaction portion disposed at a distal end of the first elongate member. The tissue interaction portion is configured to be inserted within a biological body. A second elongate member is movably disposed within a lumen defined by the first elongate member. The second elongate member has a threaded exterior surface. A drive motor is coupled to the first elongate member and coupled to the second elongate member. The drive motor is configured to rotate the first elongate member in a first direction and configured to rotate the second elongate member in a second direction opposite the first direction. The tissue interaction portion is configured to disrupt tissue when disposed into the biological body and when the first elongate member is rotated.

In some embodiments, an apparatus includes a first elongate member having a side wall with an opening and a tissue interaction member disposed at a distal end of the first elongate member. The tissue interaction member is configured to be inserted into a biological body. A second elongate member is movably disposed within a lumen defined by the first elongate member and has a threaded exterior surface. A reservoir is coupled to the first elongate member, and the opening of the first elongate member is in fluid communication with the reservoir. The tissue interaction member is configured to disrupt tissue when disposed within the biological body and when the first elongate member is rotated. The second elongate member is configured to deposit disrupted tissue fragments through the opening in the first elongate member and within the reservoir when the second elongate member is rotated relative to the first elongate member.

In some embodiments, an apparatus includes a first elongate member that defines a lumen and a second elongate member movably disposed within the lumen of the first elongate member. The second elongate member has a threaded exterior surface and defines a lumen. The threaded exterior surface includes helical threads having a direction associated with a direction of rotation of the second elongate member. A third elongate member is movably disposable within the lumen of the second elongate member. The third elongate member is movable between a first configuration in which a distal end portion of the first elongate member has a first curvature and a second configuration in which the distal end portion of the first elongate member has a second curvature different than the first curvature. The first elongate member, the second elongate member and the third elongate member collectively are configured to be inserted into a biological body when the third elongate member is in the first configuration. The distal end portion of the first elongate member is movable to the second curvature while disposed within the biological body.

It is noted that, as used in this written description and the appended claims, the singular forms "a," "an" and "the" include plural referents unless the context clearly dictates otherwise. Thus, for example, the term "a lumen" is intended to mean a single lumen or a combination of lumens. Furthermore, the words "proximal" and "distal" refer to direction closer to and away from, respectively, an operator (e.g., surgeon, physician, nurse, technician, etc.) who would insert the medical device into the patient, with the tip-end (i.e., distal end) of the device inserted inside a patient's body. Thus, for example, the end inserted inside a patient's body would be the distal end of the medical device, while the end outside a patient's body would be the proximal end of the medical device.

The term "tissue" is used herein to mean an aggregation of similarly specialized cells that are united in the performance of a particular function. For example, a tissue can be a soft tissue area (e.g., a muscle), a hard tissue area (e.g., a bone structure), a vertebral body, an intervertebral disc, a tumor, etc. The terms "body" and "biological body" are also referred to herein to have a similar meaning as the term tissue.

The term "cutting portion" is used here to mean a component of an apparatus having at least one cutting surface and being configured to, for example, cut, sever, disrupt, cleave, scrape, tear or debulk tissue. The cutting portion can be, for example, a cutting surface disposed on an elongate body, such as a cutting surface (e.g., serrations) disposed on an edge of an expandable portion of an elongate body. The cutting portion can also be a separate component coupled to a medical device.

The term "sheath" is used here to mean a component of the apparatus having one or more passageways configured to receive a device or other component. For example, a sheath can be substantially tubular. A sheath can be a variety of different shapes and size, such as having a round, square, rectangular, triangular, elliptical, or octagonal inner and/or outer perimeter. The sheath can be, for example, a cannula.

FIG. 1 is a schematic illustration of an embodiment of a medical device. A medical device 20 can include a drive mechanism 15, a first elongate member 22, a second elongate member 28 and a tissue interaction member 26. The second elongate member 28 can be movably disposed within a lumen of the first elongate member 22 and includes a threaded portion (not shown in FIG. 1) defined on an exterior surface of the second elongate member 28. For example, the second elongate member 28 can be an Archimedes screw. As described in more detail below, the second elongate member 28 can be used to transfer tissue fragments through the lumen of the first elongate member 22 as the second elongate member 28 is rotated relative to the first elongate member 22.

The drive mechanism 15 can include a gear mechanism 17 and a drive motor 24. The gear mechanism 17 can be coupled to both the first elongate member 22 and the second elongate member 28. The gear mechanism 17 and the drive motor 24 can each be disposed at least partially within a housing (not shown in FIG. 1). The drive motor 24 can be used to rotate the first elongate member 22 and the second elongate member 28. For example, the drive motor 24 can engage gears (not shown in FIG. 1) of the gear mechanism 17 that can, in turn, actuate rotation of the first elongate member 22 and the second elongate member 28. In some embodiments, the drive motor 24 and gear mechanism 17 can rotate the first elongate member 22 in a first direction (e.g., clockwise) while simultaneously rotate the second elongate member 28 in a second opposite direction (e.g., counter-clockwise). In an alternative embodiment, the drive mechanism 15 can rotate a single elongate member (e.g., elongate member 22), and the other elongate member (e.g., elongate member 28) can be rotated via gears coupled to the two elongate members. Specific details regarding the components and function of the drive mechanism 15 (e.g., drive motor 24 and gear mechanism 17) are described in more detail below with reference to specific embodiments.

The drive motor 24 can be coupled to a power source (not shown) to allow for automated actuation of the first elongate member 22 and the second elongate member 28. For example, the drive motor 24 can be coupled to a battery or battery pack disposed within or coupled to the housing of the medical device 20. In some embodiments, the drive motor 24 is coupled to a power cord configured to be coupled to an external power source (e.g., a wall outlet). The drive motor 24 can be actuated between an on position or an off position with, for example, a button or switch (not shown in FIG. 1) accessible on an exterior of the housing.

In some embodiments, the medical device 20 also includes a sheath 30 coupled to an actuation mechanism 32 (also referred to herein as "actuator"). The actuation mechanism 32 can include a lever 34 coupled to a handle 26. In some embodiments, the handle 26 is incorporated with the housing (e.g., formed monolithically with the housing) of the medical device 20. The first elongate member 22 can be disposable within a lumen defined by the sheath 30. The actuation mechanism 32 can be used to move the sheath 30 proximally and distally relative the first elongate member 22. For example, the sheath 30 can translate along a path defined by a centerline or a longitudinal axis of the first elongate member 22. In alternative embodiments, the first elongate member 22 can be configured to move relative to the sheath 30 (e.g., the sheath 30 is stationary). In some embodiments, a sheath is provided that is slidably disposed over the first elongate member that can be manually translated proximally and distally.

The tissue interaction member 26 is disposed at a distal end portion of the first elongate member 22 and is configured to be inserted into a biological body, such as a vertebra or an intervertebral disc. The tissue interaction member 26 can be coupled to the first elongate member 22 or formed monolithically with the first elongate member 22. The tissue interaction member 26 can be configured with a variety of different shapes, sizes, and functions to perform a variety of different medical procedures. For example, the tissue interaction member 26 can be used to perform a medical procedure within the biological body, such as, disrupting tissue, extracting tissue, drilling in bone, inserting a bone screw, etc. In some embodiments, the tissue interaction member 26 can be, for example, an expandable member. In some embodiments, the first elongate member 22 is tubular (e.g., defines an inner lumen) and the tissue interaction member 26 is formed by laser cutting side walls of the first elongate member 22 and shape-setting (e.g., heat-setting) the tissue interaction member 26 into an expanded configuration as described in more detail below.

A tissue interaction member 26 that is expandable (also referred to herein as "expandable member" or "expandable tissue interaction member") can include multiple arms or tines that can be formed, for example, as described above, by laser cutting side walls of the first elongate member 22. The multiple arms can be deformable. The multiple arms can extend or spiral outward from a tubular member such as the first elongate member 22. The expandable tissue interaction member 26 and/or the first elongate member 22 can be formed with, for example, a shape-memory material (e.g., nitinol or superelastic nitinol) such that the arms of the expandable tissue interaction member 26 can be biased into an expanded configuration by shape-setting the expandable tissue interaction member 26. In some embodiments, the arms have a flared shape when in the expanded configuration (e.g., an unrestrained, biased configuration) in that the arms collectively expand to an open configuration and the individual arms each have a curved or flared shape along its length. Such a flared shape is shown, for example, in FIG. 12, and discussed in greater detail below. In the expanded configuration, the arms can flare open to define an outer diameter that is, for example, 2 to 4 times larger than an outer diameter of remaining portions of the first elongate member 22. In some embodiments, the arms are in a spiral configuration as shown, for example, in FIG. 6, and discussed in greater detail below. In some embodiments, the arms can have a substantially linear or straight configuration when expanded (not shown).

The arms of an expandable tissue interaction member 26 can collectively be moved to a collapsed configuration by constraining the arms within, for example, the lumen of the sheath 30 described above. In some embodiments, the actuation mechanism 32 can move the sheath 30 proximally and distally relative the first elongate member 22 as described above such that the tissue interaction member 26 is moved from a position in which it is disposed within the sheath 30, and a position in which it is disposed outside of a distal end of the sheath 30. Thus, as the sheath 30 is moved distally and proximally, the tissue interaction member 26 is moved between its collapsed configuration (within the sheath 30) and expanded configuration (outside the sheath 30), respectively. As described herein, both the expandable tissue interaction member 26 and the arms of the expandable tissue interaction member 26 are referred to as having an expanded configuration and a collapsed configuration. The first elongate member 22 and/or medical device 20 can also be referred to as having a collapsed configuration and an expanded configuration.

The arms of the expandable tissue interaction member 26 can also include a cutting portion configured to cut or tear tissue. For example, the arms can include serrations along one or more edge of the arms. The serrations can cut or tear tissue within the biological body, for example, when the arms of the expandable tissue interaction member 26 are moved within the biological body. In some embodiments, serrations are included only on a leading edge of the arm during rotation of the expandable tissue interaction member 26. The serrations can be formed, by laser cutting. For example, when arms are formed by laser cutting side walls of the first elongate body 22, as described above, the serrations can also be cut. The serrations can vary in size and quantity as described in more detail below.

In some embodiments, the medical device 20 also includes a reservoir 38 that can be used to hold tissue fragments drawn into the medical device with the second elongate member 28. The reservoir 38 can be incorporated within, or be coupled to the housing of the medical device 20. The first elongate member 22 can include one or more openings (not shown in FIG. 1) that are in fluid communication with the reservoir 38. As the second elongate member 28 is rotated within the lumen of the first elongate member 22, the second elongate member 28 can draw or transfer tissue fragments (e.g., tissue fragments produced with the tissue interaction member 26) through the lumen of the first elongate member 22, through the opening of the first elongate member 22 and into the reservoir 38.

In some embodiments, a flexible member (not shown in FIG. 1) is coupled to a distal end portion of the first elongate member 22. The flexible member is formed such that it can be moved between a first configuration in which it exhibits a first curvature (e.g., a substantially straight or linear configuration) and a second configuration in which it exhibits a second curvature (e.g., a substantially curved configuration). A steering mechanism 40 is used to move the flexible member between the two configurations and thus, steer or maneuver the first elongate member 22 within a biological body as described in more detail below. A proximal end of the flexible member can be coupled to a distal end of the first elongate member 22, or the flexible member and the first elongate member 22 can be formed as one component (e.g., monolithically formed). The tissue interaction member 26 can be coupled to a distal end portion of the flexible member such that when the flexible member is maneuvered within a biological body, the tissue interaction member 26 will in turn be moved within the biological body.

In one embodiment, the steering mechanism 40 can include a steering member (not shown in FIG. 1) disposed within a lumen defined by the second elongate member 28. The steering member can be, for example, a steering rod. The steering member can be formed with, for example, a shape-memory material such as nitinol or super-nitinol. The steering mechanism 40 can include, for example, a steering knob (not shown in FIG. 1), and a splined shaft (not shown in FIG. 1) coupled to the second elongate member 28. The steering mechanism 40 can be actuated to move the second elongate member 28 proximally and distally relative to the steering member while simultaneously maintaining rotation of the second elongate member 28. The specific operation of the steering mechanism 40 is described in more detail below with reference to specific embodiments.

In one example use of the medical device 20, a distal end portion of the medical device 20 can be percutaneously inserted into a biological body, such as a vertebral body or an intervertebral disc. In this example, the tissue interaction member 26 is referred to as an expandable member as described above having collapsible arms. The distal end portion of the medical device 20 is inserted into the biological body with the expandable member in a collapsed configuration (e.g., the arms collapsed within the sheath 30). In some embodiments, the medical device 20 is inserted through a separate cannula used to gain access to a tissue site rather than the sheath 30. The expandable member can be moved to an expanded configuration while within the biological body and used to disrupt, cut or tear tissue within the biological body. For example, in an embodiment including a sheath 30, the medical device 20 can be actuated, for example, using the lever 34 to actuate the actuation mechanism 24, and translate the sheath 30 distally such that the expandable member is disposed within the sheath 30 for insertion into the biological body. After insertion, the sheath can be translated proximally such that the expandable member is moved to the expanded configuration. The drive mechanism 15 can then be actuated to cause automated rotation of the first elongate member 22 and the second elongate member 28. As the first elongate member 22 is rotated, the expandable member will also rotate such that the arms of the expandable member will scrape, disrupt or otherwise cut tissue within the biological body. As the expandable member disrupts tissue within the biological body, tissue fragments will be drawn through the lumen of the first elongate member 22 with the rotation of the second elongate member 28.

In an embodiment of the medical device 20 having a reservoir 38, the tissue fragments can be drawn into the interior region of the reservoir 38 as described above. In some embodiments, the reservoir 38 can be configured to be coupled to a suction source (not shown in FIG. 1). For example, the reservoir 38 includes a port (not shown in FIG. 1) in fluid communication with the interior region of the reservoir 38. A suction source can then be coupled to the port of the reservoir 38. The disrupted tissue can then be drawn or suctioned out of the reservoir 38 either simultaneously with the disrupting, or after the disruption procedure has been completed. After the desired amount of disruption of tissue and/or removal the desired amount of disrupted tissue has been performed, the medical device 22 can be removed form the biological body. For example, the expandable member can be moved to the collapsed configuration by actuation of the sheath 30 (e.g., translate the sheath 30 distally) to allow the medical device 20 to be removed from the biological body.

In alternative embodiments that do not include a reservoir 38, a separate suction device can be inserted through the lumen of the first elongate member 22 and used to suction the disrupted tissue. Other procedures such as a procedure to inject bone cement into a cavity produced within the biological body by removal of disrupted tissue can also optionally be performed.

Having described above various general examples, several examples of specific embodiments are now described. These embodiments are only examples, and many other configurations and uses of the medical devices described herein are contemplated.

FIGS. 2-5 illustrate a medical device according to an embodiment. As shown in FIG. 2, a medical device 120 includes a sheath 130 coupled to a housing 142 that includes a handle 136. A first elongate member 122 is disposed within a lumen 133 of the sheath 130 as shown in FIG. 5, and a second elongate member 128 is disposed within a lumen 125 of the first elongate member, as shown in FIGS. 4 and 5. The first elongate member 122 includes a tissue interaction member 126 at a distal end of the first elongate member 122. In this embodiment, the tissue interaction member 126 is an expandable member that includes multiple arms or tines 127, formed for example, by laser cutting longitudinal slits along a wall of the first elongate member 122. The second elongate member 128 includes a threaded outer surface (shown in FIG. 5) with threads angled in a direction of rotation of the second elongate member 128.

As shown in FIGS. 3 and 4, the medical device 120 also includes a drive mechanism 115 that includes a drive motor 124 (shown schematically in FIGS. 4 and 5) and a gear mechanism 117. The gear mechanism 117 includes a first bevel gear 137 and a second bevel gear 139. A drive bevel gear 147 is coupled to a drive pin 141 of the drive motor 124, and matingly engages the first bevel gear 137 and the second bevel gear 139. The first bevel gear 137 has threads angled in a first direction, and the second bevel gear 139 has threads angled in an opposite direction.

The first bevel gear 137 is coupled to the first elongate member 122, and the second bevel gear 139 is coupled to the second elongate member 128 (shown in FIGS. 4 and 5). The drive motor 124 is configured to rotate the drive pin 141 and the drive bevel gear 147. As the drive bevel gear 147 rotates, the first bevel gear 137 will rotate in a first direction (e.g., clockwise) based on the direction of the threads of the first bevel gear 137, and the second bevel gear 139 will rotate in a second direction opposite the first direction of the first bevel gear 137 (e.g., counter-clockwise) based on the direction of the threads of the second bevel gear 139. Thus, because the first bevel gear 137 and the second bevel gear 139 are coupled to the first elongate member 122 and the second elongate member 128, respectively, the first elongate member 122 will rotate in the first direction, and the second elongate member 128 will rotate in the second direction. The first elongate member 122 rotates within the lumen 133 of the sheath 130, and the second elongate member 128 rotates within the lumen 125 of the first elongate member 122.

The drive motor 124 can be powered with a battery or battery pack 149 (only a top portion of which is shown in FIG. 3) disposed within the handle 136. The drive motor 124 can also be coupled to a button or switch 150. The switch 150 can be actuated by a user to turn the drive motor 124 on and off. The drive motor 124 can alternatively be coupled to a power cord to allow for the drive motor 124 to be coupled to an external power source such as a wall outlet.

The sheath 130 is coupled to an actuation mechanism 132 (see FIG. 3) that includes the handle 136 and a lever 134. The actuation mechanism 132 also includes a return spring 143, a face clutch 144 and a flange 145, as shown in FIGS. 3 and 4. The flange 145 can be monolithically formed with the sheath 130 or provided as a separate component that is coupled to the sheath 130. A top portion 135 of the lever 134 straddles the sheath 130, as shown in FIGS. 3 and 4, and engages the face clutch 144. The face clutch 144 also engages the first elongate member 122. The return spring 143 is disposed about a proximal end portion of the sheath 130. The return spring 143 pushes against the flange 145 and top portion 135 of the lever 134, which biases the lever 134 away from the handle 136. In this position, the sheath 130 is translated proximally such that the tissue interaction member 126 is disposed outside a distal end portion 131 of the sheath 130 as shown in FIGS. 2 and 5. When the lever 134 is actuated (e.g., pulled toward the handle 136), the lever 134 pivots about a pivot joint 146 such that the top portion 135 of the lever 134 is moved distally and exerts an axial force on the flange 145. As the axial force is exerted on the flange 145, the sheath 130 moves distally relative to the first elongate member 122. The force exerted by the top portion 135 on the flange 145 also compresses the return spring 143. With the lever 134 actuated (squeezed toward the handle 136), the distal end portion 131 of the sheath 130 will at least partially cover the tissue interaction member 126 (not shown), which will collapse the tissue interaction member 126 (see FIG. 6). In addition, the top portion 135 of the lever 134 engages the face clutch 144, which prevents the first elongate member 122 from rotating when the sheath 130 is translated.

A reservoir 138 is coupled to the housing 142 with a threaded coupling 155 (see FIG. 4) and has a port 148 coupled thereto. As shown in FIG. 4, the sheath 130 defines multiple openings 152 in a side wall of the sheath 130, and the first elongate member 122 defines multiple openings 154 in a side wall of the first elongate member 122. The openings 152 are in fluid communication with the lumen 131 of the sheath 130 and the reservoir 138. The openings 154 are in fluid communication with the lumen 125 of the first elongate member 122 and the lumen 131 of the sheath 130. The port 148 can be coupled to a suction source (not shown) with for example, a suction line, hose or conduit, such that tissue fragments that have been drawn into the reservoir 138 (described in more detail below) can be removed from the reservoir 138. The port 148 can also be used for introducing a fluid such as a saline solution through the medical device 120 and into the biological body. Such irrigation can be performed before, during or after the medical device 120 disrupts tissue. In some embodiments, the port 148 can include a one-way valve, such as a pressure relief valve, configured to allow for air to escape from within the reservoir 138. For example, in some embodiments, as tissue fragments are drawn into the reservoir 138, air within the reservoir 138 may become pressurized. A pressure relief valve can be used to allow for a one-way flow of air to exit the reservoir 138.

The first elongate member 122 can be formed with, for example, a shape-memory material (e.g., nitinol or superelastic-nitinol) such that the arms 127 of the tissue interaction member 126 (also referred to herein as expandable member 126) can be biased into an expanded configuration. Each of the arms 127 when in the expanded configuration are curved or flared in a lengthwise or longitudinal direction, but in other embodiments, the arms 127 can be substantially straight in a longitudinal direction, and/or have other shapes and/or configurations. In this embodiment, the arms 127 of the expandable member 126 have a spiral configuration.

Figure 7:
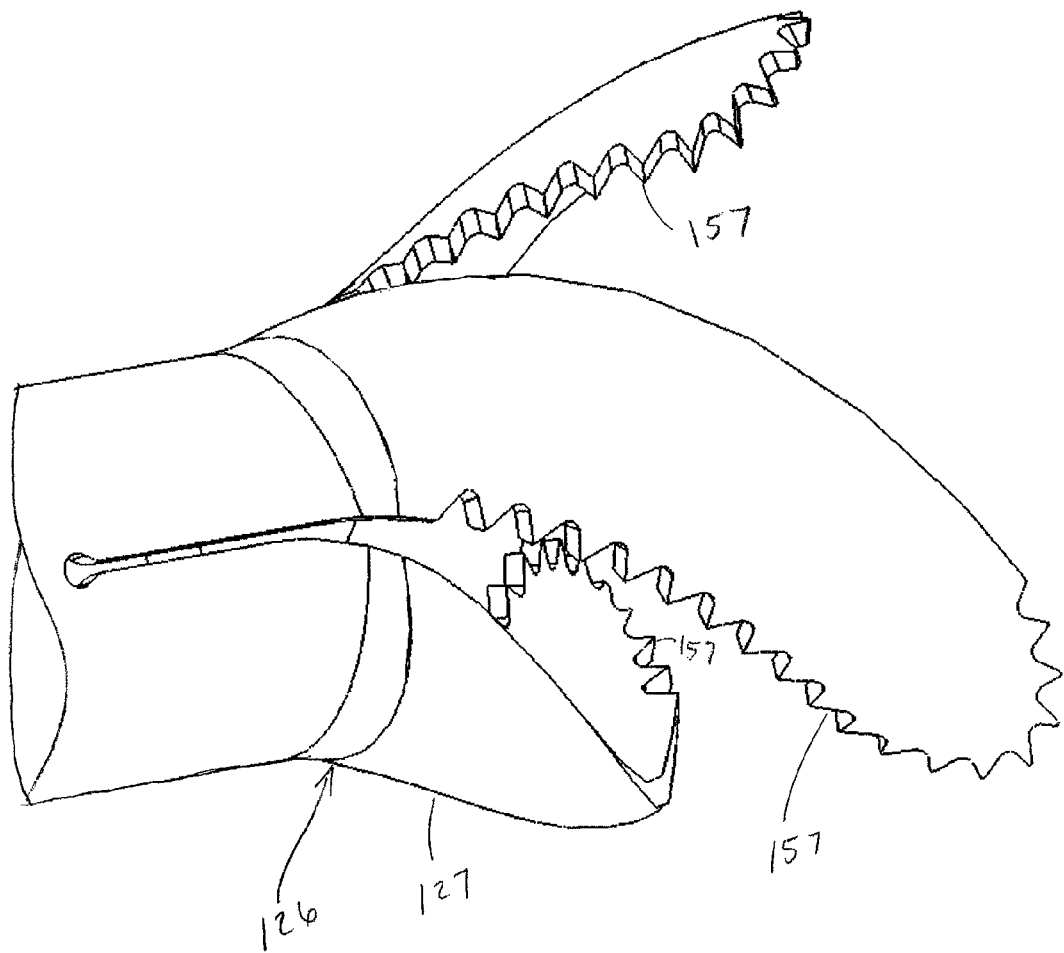
FIG. 7 is a side perspective view of a portion of the expandable member of the medical device of FIG. 2, shown with the tissue interaction member in an expanded configuration.
Figure 8:
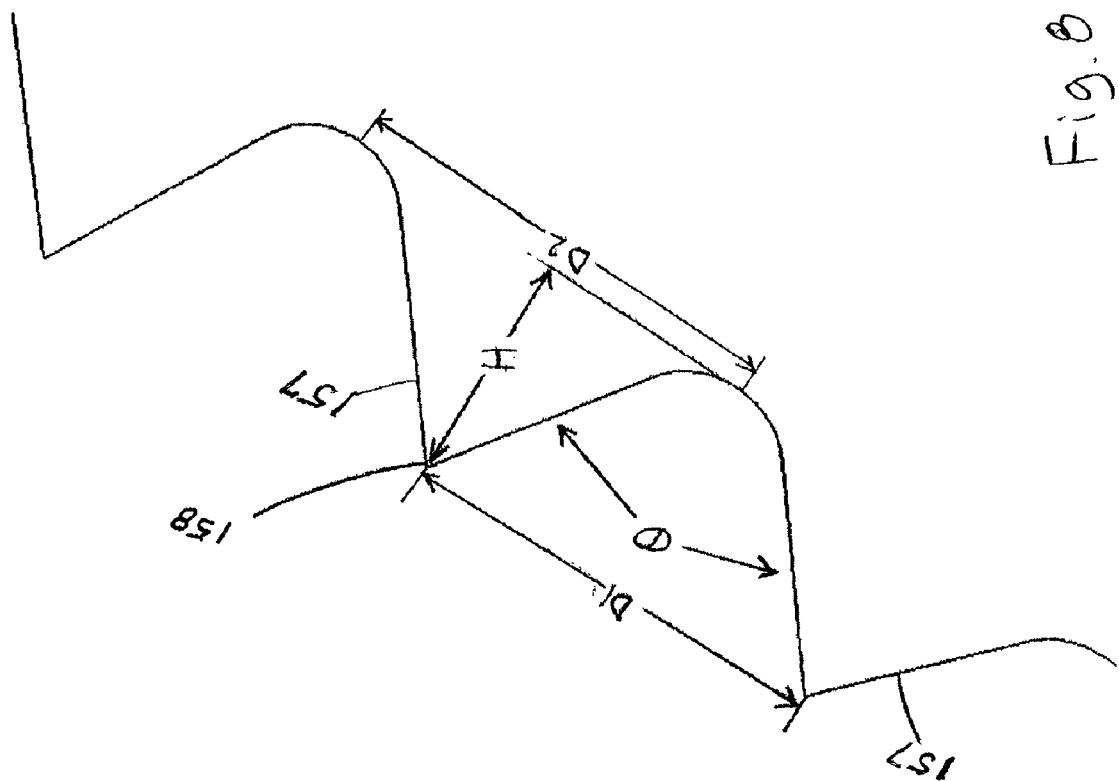
FIG. 8 is a schematic illustration of serrations according to another embodiment.

The expandable member 126 can be moved from the expanded configuration (shown in FIGS. 2, 5 and 7) to a collapsed configuration when it is constrained within the sheath 130 (shown in FIG. 6) as described above. The expandable member 126 in its expanded configuration defines an interior region 156 that is in communication with the lumen 125 of the first elongate member 122 as shown in FIGS. 5 and 8. The expandable member 126 in its expanded configuration has a greater size than an outer diameter of the elongate body 122.

The arms 127 can each include a cutting portion along an edge of that arm 127. For example, the arms 127 each can have a sharpened edge or, as shown in FIG. 7, the arms 127 each can include serrations 157 along an edge of that arm 127. The arms 127 shown in FIGS. 2 and 5 are shown without serrations for illustration purposes only. In this embodiments, the serrations 157 are only along a leading edge of the arms 127 in a direction of rotation of the arms 127. In this example embodiment, the elongate member 122 and expandable member 126 are configured to rotate in a clock-wise direction as indicated by the leading edge on which the serrations 157 are disposed. In alternative embodiments, the arms each can also include serrations along a trailing edge of that arm in addition to the leading edges. In other alternative embodiments, the arms each can include serrations along the entire edge of that arm. The serrations 157 (also referred to herein as "teeth") can be formed by laser cutting, for example, when the arms 127 are laser cut in the side wall of the elongate member 122. As shown in FIG. 8, each individual serration 157 can have, for example, a height H that is $1/10^{th}$ a width (not shown in FIG. 8) of the particular arm 127 on which the serration 157 is formed. The distance or spacing D1 between individual serrations 157 measured from peak-to-peak can substantially equal, for example, a distance D2 measured valley-to-valley between the serrations. An angle θ between the edges of consecutive serrations 157 can be, for example, 60 degrees. An end portion 158 of the serrations 157 can be, for example, substantially flat or linear, can form a sharp tip (as shown in FIG. 8), or can be rounded or curved.

Figure 9:
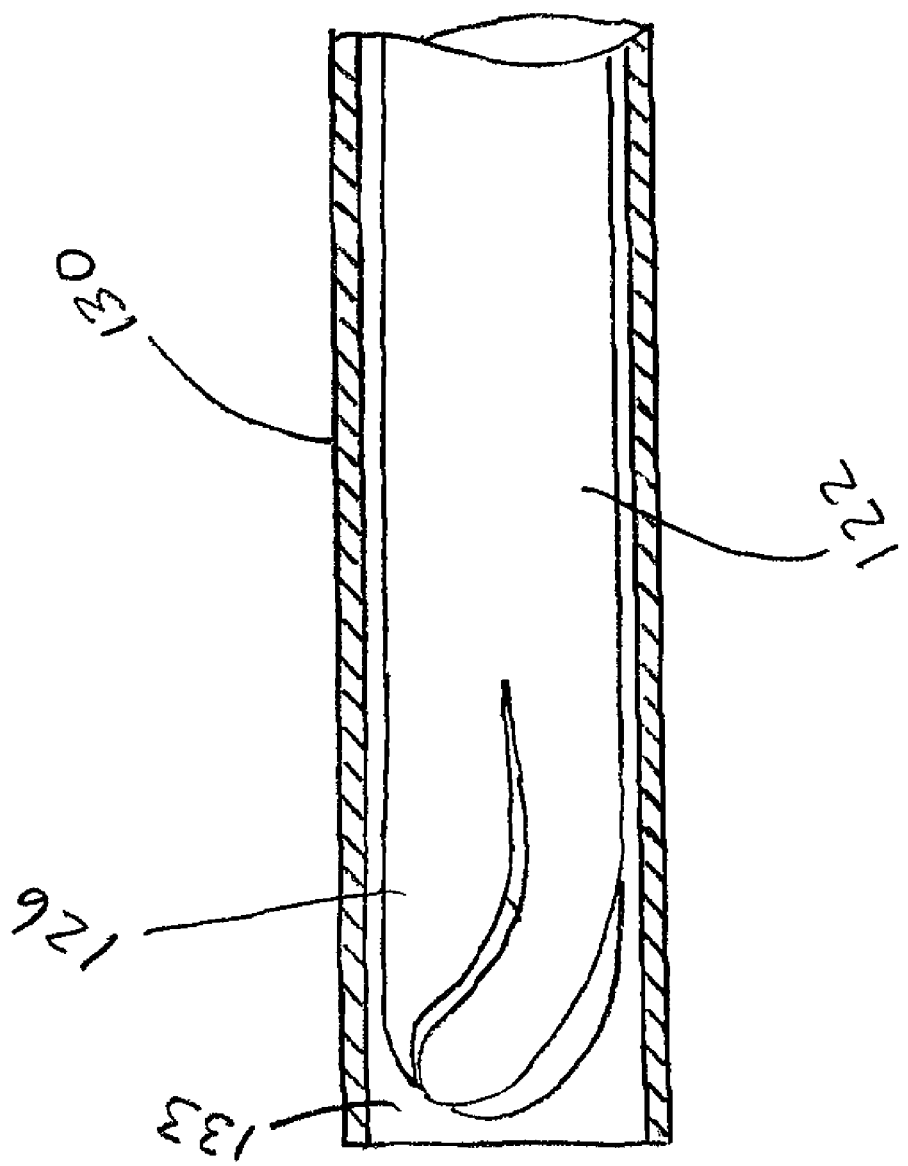
FIG. 9 is a distal end view of the expandable member of FIG. 7 shown without serrations.

FIG. 9 is a distal end view of the expandable member 126 (shown without serrations 157 for illustration purposes) in its expanded configuration. As shown in FIG. 9, the interior region 156 defined by the arms 127 is in communication with the lumen 125 of the first elongate member 122. FIG. 9 also illustrates a flared shape of the arms 127 that is counterclockwise corresponding to a clockwise rotation of the spiral configuration. Alternatively, arms can be formed to flare clockwise if an opposite drive direction (e.g., a counterclockwise direction) is desired.

The medical device 120 can be used for a variety of different types of medical procedures. In one example, the medical device 120 can be used to treat a herniated intervertebral disc. For example, the medical device 120 can be used to disrupt and remove nucleus material from an interior of an intervertebral disc. An access path into the intervertebral disc can be made, for example, with a stylet or other access tool through, for example, Kambin's triangle. The medical device 120 can be inserted through the access path and into the nucleus of the intervertebral disc with the sheath 130 disposed distally over at least a portion of the expandable member 126. For example, as described above, the lever 134 can be squeezed such that the sheath 130 is translated distally. The medical device 120 can also optionally be used in conjunction with an access cannula as described below (e.g., access cannula 572 shown in FIGS. 21 and 22). In such a case, the access cannula is inserted into the access path, and the medical device 120 is inserted through a lumen of the access cannula.

Another example of a device that can be used to gain access to an intervertebral disc is described in U.S. patent application Ser. No. 11/250,617, filed Oct. 17, 2005, and entitled "Balloon Assisted Apparatus and Method for Accessing an Intervertebral Disc" ("the '617 application"), the entire disclosure of which is incorporated herein by reference. As described in the '617 application, a device having a sharp tip and a balloon coupled thereto can be inserted through a lumen of a cannula with the balloon in a collapsed configuration. The sharp tip can penetrate the annular wall and the device can be positioned such that the balloon is disposed within the annulus material of the intervertebral disc. The balloon can then be expanded such that the annulus material is distracted by the balloon forming an access opening through the annular wall sufficient to insert the cannula.

Other example procedures to gain access to an intervertebral disc are described in U.S. patent application Ser. No. 10/825,961, filed Apr. 16, 2004, and entitled "Spinal Diagnostic Methods and Apparatus" ("the '961 application"), the entire disclosure of which is hereby incorporated by reference. For example, in one embodiment of the '961 application, an introducer device and a pointed obturator are inserted into an intervertebral disc. The pointed obturator is used to penetrate the annular wall of the intervertebral disc and then removed. A guidewire is then inserted through the introducer and used to guide a cannula through the introducer and into the intervertebral disc. In another example described in the '961 application, a catheter having a stylet is passed through an introducer device and into an intervertebral disc without the use of a guidewire.

When a distal end of the medical device 120 is in a desired position within the nucleus of the intervertebral disc, the lever 134 can be released. This will cause the sheath 130 to move proximally relative to the elongate member 122 such that the expandable member 126 is unrestrained and can move to its expanded configuration. With the expandable member 126 in its expanded configuration, the drive mechanism 115 of the medical device 120 can be turned on as described above, by actuating the switch 150. The drive mechanism 115 will then rotate the first elongate member 122 and the expandable member 126 within the nucleus of the intervertebral disc. Simultaneously, the drive mechanism 115 will rotate the second elongate member 128 in an opposite direction of the first elongate member 122. As the expandable member 126 rotates, the serrations 157 on the arms 127 will cut, tear or otherwise disrupt tissue within the nucleus of the intervertebral disc. The medical device 120 can also be translated proximally and distally while the expandable member 126 is rotated. Such translation can form a channel of disrupted nucleus material within the intervertebral disc. The rotation of the second elongate member 128 will draw tissue fragments produced by the expandable member 126 through the lumen 125 of the first elongate member 122 and into the reservoir 138. For example, the tissue fragments can be drawn through the lumen 125, through the openings 154 of the first elongate member 122, through the openings 152 of the sheath 130, and into the reservoir 138.

When the user (e.g., medical practitioner) is satisfied with the amount of tissue that has been disrupted and/or removed, the medical device 120 is removed from the intervertebral disc. For example, the lever 134 can be squeezed to cause the sheath 130 to move distally over at least a portion of the expandable member 126 such that the expandable member 126 is moved to its collapsed configuration With the expandable member 126 in the collapsed configuration, the medical device 120 is removed from the intervertebral disc. To remove the disrupted nucleus material (e.g., tissue fragments) from within the reservoir 138, a suction source can be coupled to the reservoir 138 as described above.

In some cases it may be desirable to apply suction to the reservoir during the procedure to disrupt the tissue within the intervertebral disc. For example, the suction source can be coupled to the reservoir 138 and actuated to apply suction within the reservoir to help draw the tissue fragments into the reservoir.

In some embodiments, the expandable member 126 can be used to capture and remove the disrupted nucleus material. For example, the expandable member 126 can be moved to the collapsed configuration while within the nucleus by actuating the distal translation of the sheath 130 such that the expandable member 126 collapses over a portion of tissue capturing the portion of tissue within the interior region 156 of the expandable member 126. The medical device 120 can be withdrawn with the captured disrupted material.

The medical device 120 can also be used in a similar manner as a bone biopsy device. The medical device 120 can be actuated such that rotation of the expandable member 126 aids in coring a bone sample; the sheath 130 then translates over the expandable member 126 with the bone sample captured therein. The medical device 120 can be removed from the biological body with the core sample disposed within the interior region 156 of the expandable member 126. Such a biopsy procedure can be performed in hard tissue areas, such as within a bone structure (e.g., a vertebra), or soft tissue areas, such as within an intervertebral disc.

FIG. 10 illustrates an alternative embodiment of a tissue interaction member (e.g., expandable member). As with the expandable member 126, an expandable member 226 includes arms 227 formed, for example, by slits cut (e.g., laser cut) along a side-wall of an elongate member 222. The expandable member 226 can also be formed with a nitinol or superelastic nitinol shape-memory material that is heat-set into an expanded configuration. Thus, the expandable member 226 has a biased expanded configuration as shown in FIG. 10. The arms 227 can also have a curved or flared configuration as shown in FIG. 10. In this embodiment, the arms 227 of the expandable member 226 do not curve in a spiral configuration, but each include serrations 257 along an entire edge of that arm 227. The serrations 257 can be sized and configured in the same manner as described above with reference to serrations 157 (see, e.g., FIG. 8). It is to be understood that in some embodiments the arms 227 can also include serrations only along a leading edge of the arms as with expandable member 126.

The expandable member 226 can be moved from the expanded configuration to a collapsed configuration. As described above for expandable member 126, the expandable member 226 can be restrained, for example, within a sheath (e.g., sheath 130) for insertion into a biological body or tissue. When the expandable member 226 exits a distal end of the sheath, the expandable member 226 can assume its biased expanded configuration. As shown in FIG. 10, the expandable member 226 in its expanded configuration has a greater size (e.g., diameter of a circle formed by a cross-section of the distal ends of the arms) than an outer diameter of the elongate body 222. The arms 227 also define an interior region 256 that is in communication with a lumen 225 of the elongate member 222.

FIGS. 11-16 illustrate an embodiment of a medical device having a steering mechanism configured to steer a distal end portion of the medical device within a biological body. A medical device 320 includes a first elongate member 322 and a second elongate member 328 (see FIGS. 13-16) movably disposed within a lumen 325 of the first elongate member 322. The second elongate member 328 has a threaded outer surface similar to the second elongate member 128 described above. In this embodiment, a flexible member 362 is coupled to a distal end of the elongate member 322, and a tissue interaction member 326 (also referred to herein as expandable member 326) is disposed at a distal end of the flexible member 351.

The first elongate member 322 and the second elongate member 328 are each coupled to a drive mechanism 315 disposed within a housing 342. As with the previous embodiments, the housing 342 includes a handle 336, and the drive mechanism 315 is disposed within the housing 342. The drive mechanism 315 includes a drive motor 324 and gear mechanism 317 similar to those described above for medical device 120.

Figure 12:
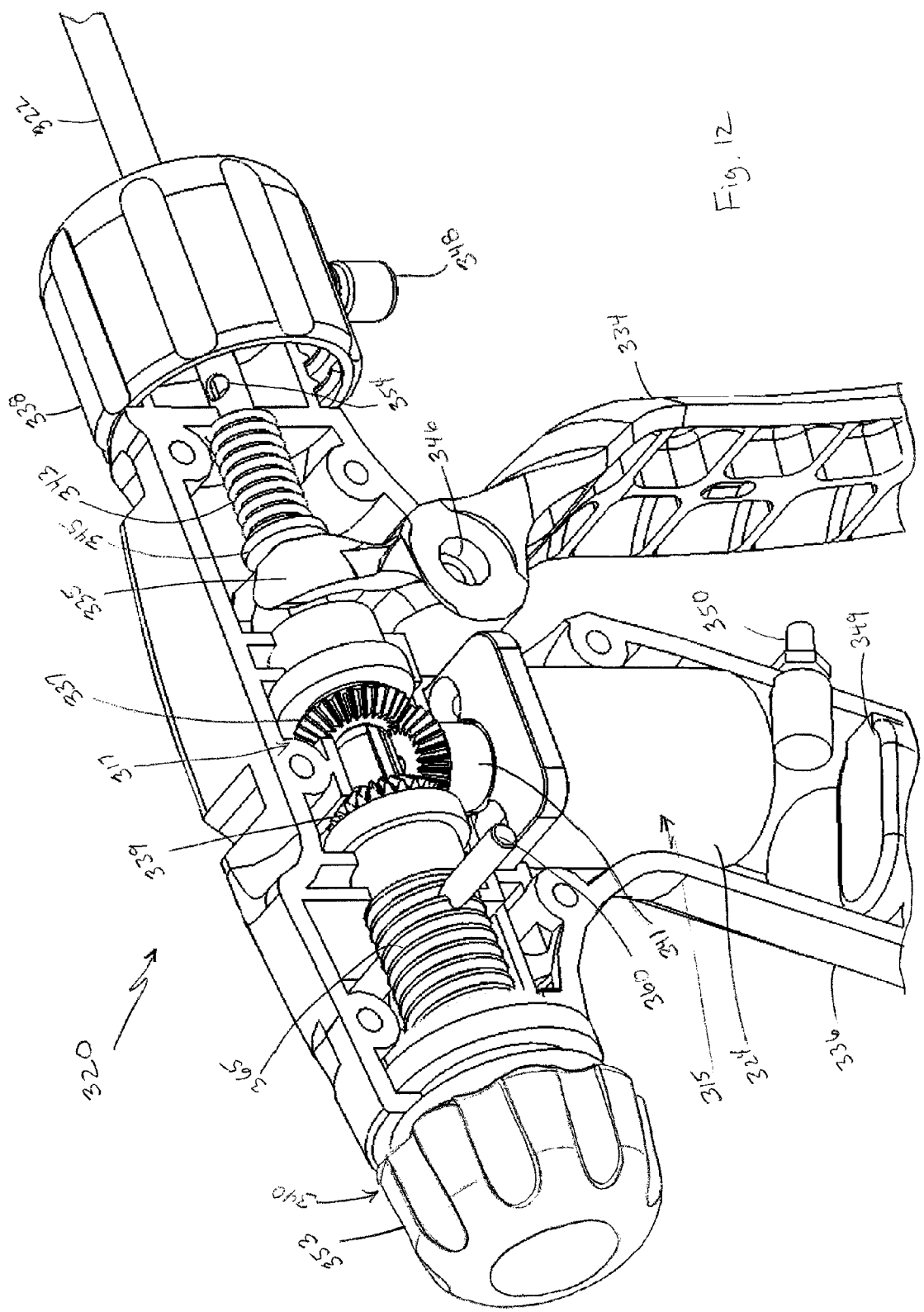
FIG. 12 is a side perspective view of a portion of the medical device of FIG. 11 shown with a portion of the housing removed.
Figure 13:
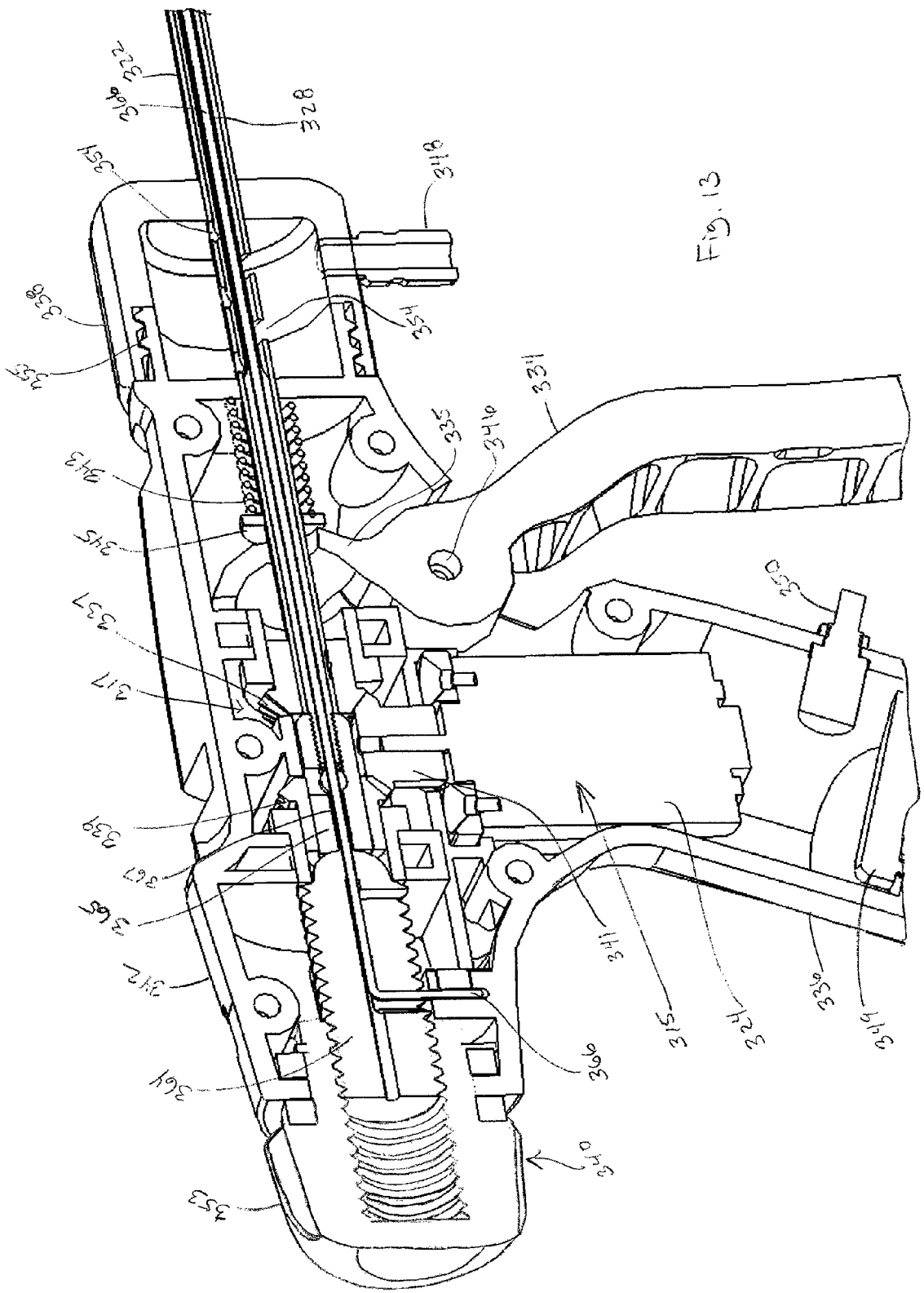
FIG. 13 is a side cross-sectional view of a portion of the medical device of FIG. 1 showing the steering mechanism in a first position.

The gear mechanism 317 includes a first bevel gear 337 and a second bevel gear 339 and a drive bevel gear 347 is coupled to a drive pin 341 of the drive motor 324, and matingly engages the first bevel gear 337 and the second bevel gear 339. The first bevel gear 337 has threads angled in a first direction, and the second bevel gear 339 has threads angled in an opposite direction. The drive mechanism 315 can be powered with a battery or battery pack 349 (a portion of which is shown in FIGS. 12 and 13) or with an external power source as described above for medical device 120. The drive motor 324 is also coupled to a button or switch 350 that can be actuated by the user to turn the drive motor 324 on and off as described in more detail below. The drive mechanism 315 can actuate the gear mechanism 317 in a similar manner as described above to rotate the first elongate member 322 and second elongate member 328. Thus, the specific details of the function and operation of the drive mechanism 315 will not be described in detail.

The medical device 320 also includes an actuation mechanism 332 used to turn the drive mechanism 315 on and off. Although not shown in this embodiment, a sheath can optionally be included on medical device 320 and the actuation mechanism 332 can be used to translate the sheath as described above for medical device 120. The actuation mechanism 332 includes the handle 336, the button 350, a lever 334, a return spring 343 and a washer 345, as shown in FIGS. 12 and 13. A top portion 335 of the lever 334 straddles the first elongate member 322, as shown in FIGS. 12 and 13. The return spring 343 is disposed about a proximal end portion of the first elongate member 422. The return spring 343 is biased such that it exerts an axial force in a proximal direction against the washer 345 and top portion 335 of the lever 334, which biases the lever 334 away from the handle 336.

When the lever 334 is actuated (e.g., pulled toward the handle 336), the lever 334 pivots about a pivot joint 346 such that the top portion 335 of the lever 334 is moved distally and exerts an axial force on the washer 345 and compresses the return spring 343. The lever 334 contacts the button 350 and turns the drive motor 324 on.

As with the previous embodiments, a reservoir 338 is coupled to the housing 342 and has a port 348 coupled thereto. As shown in FIG. 13, the first elongate member 322 defines openings 354 in a side wall of the first elongate member 322. The openings 354 are in fluid communication with the lumen 325 of the first elongate member 322 and the reservoir 338. The port 348 can be coupled to a suction source (not shown) with for example, a suction line, hose or conduit, to provide suction at the distal end portion of the medical device. As described above, suction can be applied to the reservoir 338 to remove tissue fragments that have been drawn into the reservoir 338. The port 348 can also be used for introducing a fluid such as a saline solution through the medical device 320 and into the biological body.

Figure 11:
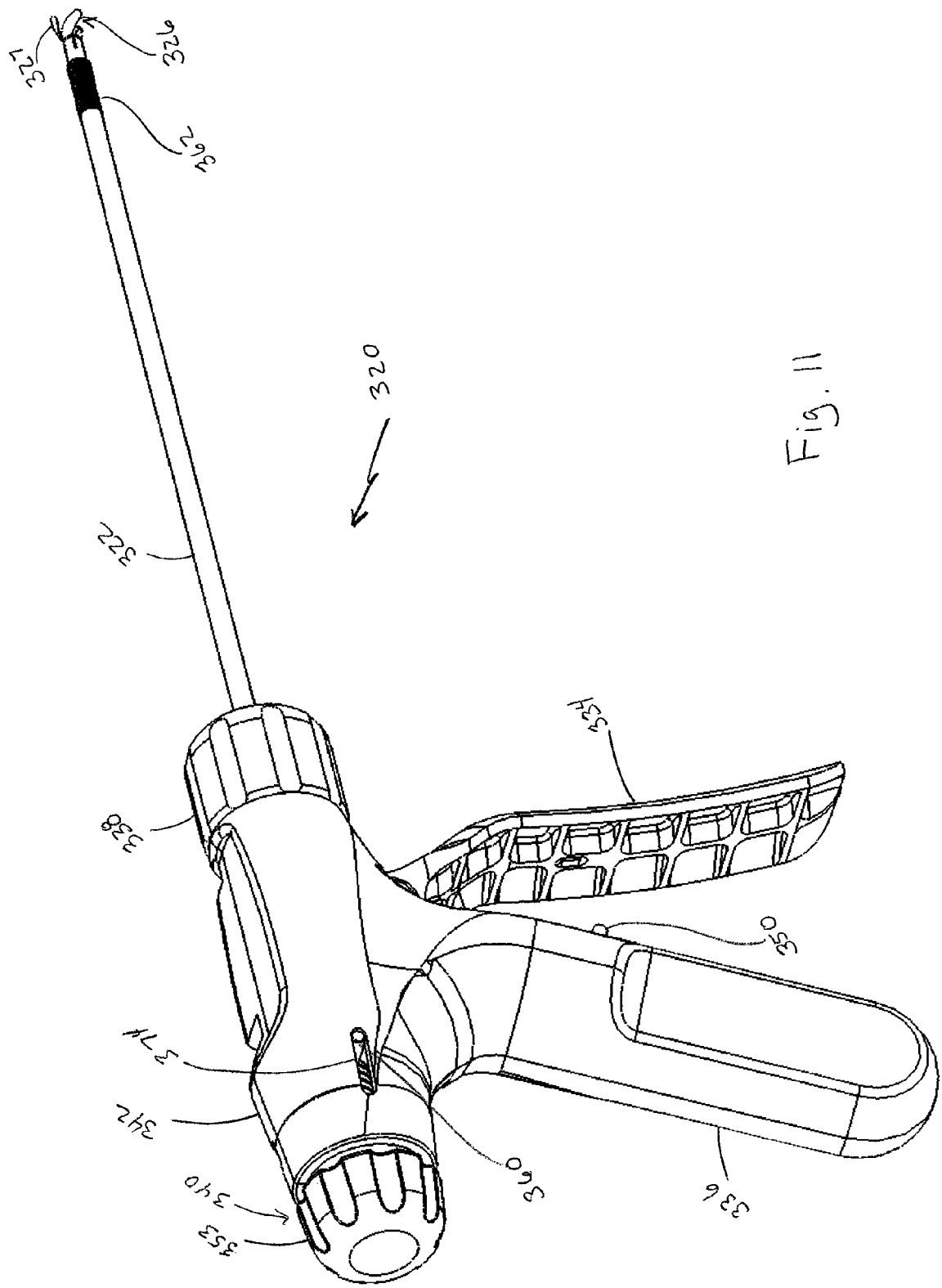
FIG. 11 is side perspective view of another embodiment of a medical device.
Figure 14:
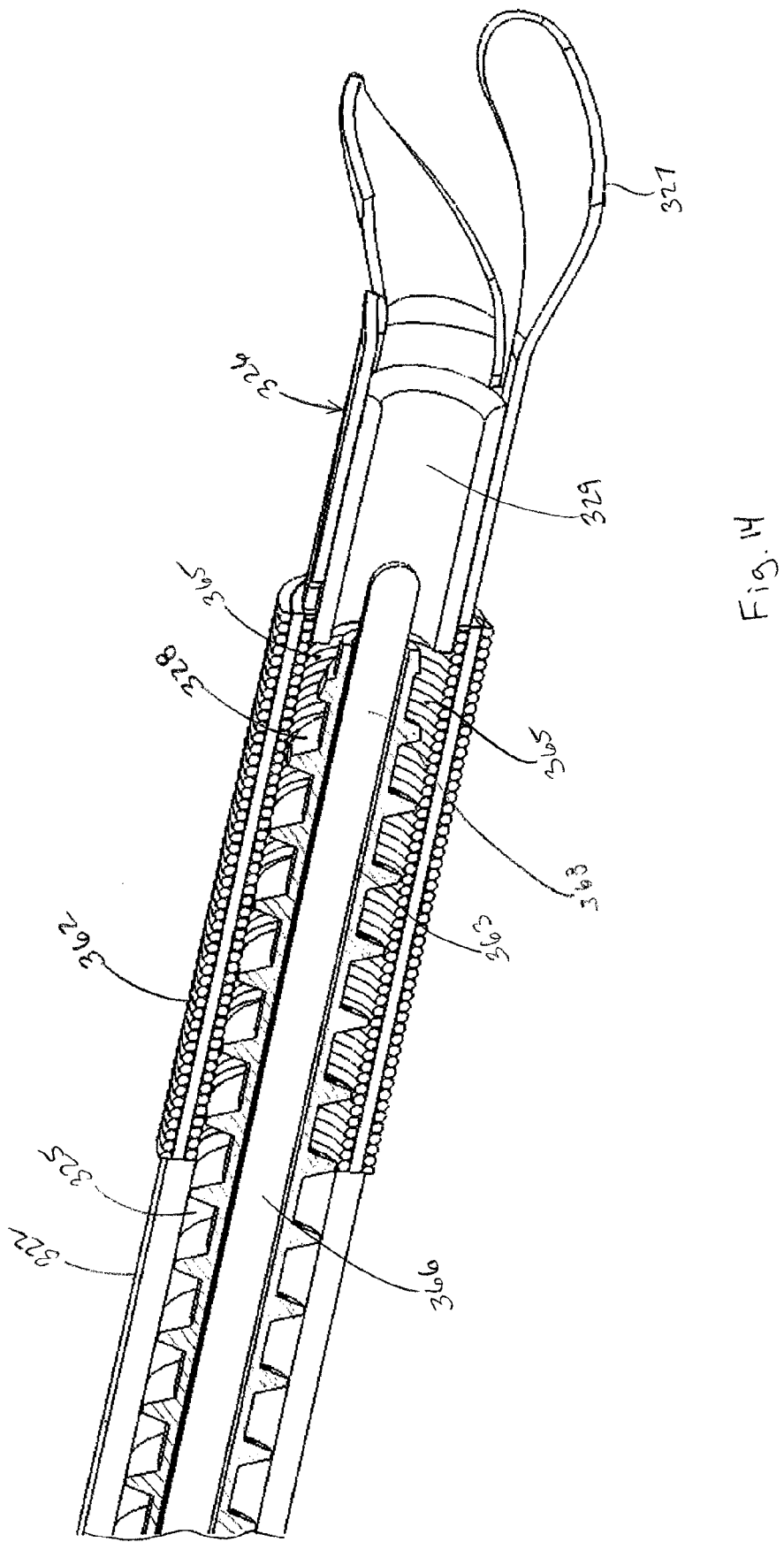
FIG. 14 is a side cross-sectional view of a distal end portion of the medical device of FIG. 1 in a first configuration.
Figure 16:
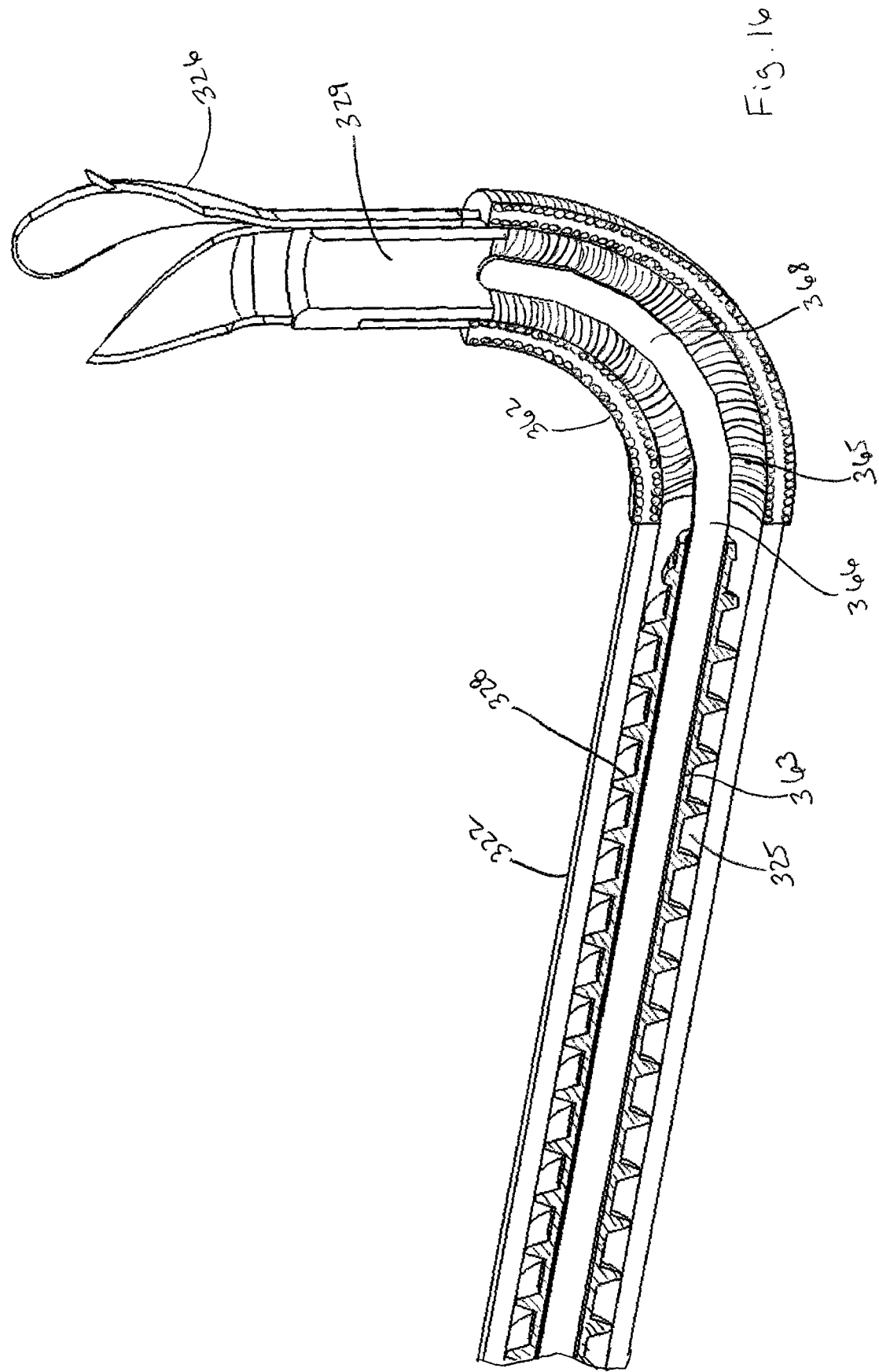
FIG. 16 is a side cross-sectional view of a distal end portion of the medical device of FIG. 1 in a second configuration.

The expandable member 326 is similar to the expandable member 126 and includes arms 327. The expandable member 326 has a biased expanded configuration as shown in FIGS. 11, 14 and 16) and can be moved to a collapsed configuration (not shown). The expandable member 326 (and arms 327) can be moved to the collapsed configuration as described above (e.g., for expandable members 126, 226) when constrained within a sheath or cannula. For example, a sheath (not shown) can be slidably placed over the first elongate member 322 such that it can be moved distally over the expandable member 326 to collapse the expandable member 326. The sheath can be slid proximally relative to the first elongate member 322 such that the expandable member 328 is disposed outside of the cannula and can assume its expanded configuration. The expandable member 326 can also include serrations (not shown), and can be used to tear, cut, or otherwise disrupt tissue as previously described. In this embodiment, the expandable member 326 is a separate component from the first elongate member 322, but can be formed in a similar manner. For example, the arms 327 of the expandable member 326 can be formed by laser cutting longitudinal slits along a tubular component formed, for example, with a shape memory material. The arms 327 can then be heat-set into a biased expanded configuration.

The flexible member 362 can be formed, for example, with a flexible cable material or spring material, such as a torque cable. In other embodiments, the flexible member 362 can be formed with a flexible material that has a substantially smooth surface. The flexible member 362 can alternatively be formed monolithically with the first elongate member 322. The flexible member 362 is formed such that it can be moved between various curvatures. For example, the flexible member 362 can be moved between a substantially straight or linear configuration as shown in FIGS. 11 and 14 and a curved configuration as shown in FIG. 16. The curvature of the flexible member 362 shown in FIG. 16 is merely an example curvature, as the flexible member 362 can be reconfigured into multiple different curvatures as desired. The flexible member 362 is used in conjunction with a steering mechanism 340 (described below), which is used to move the flexible member 362 between the its different curvature to steer or maneuver a distal end portion of the medical device 320 within a biological body.

The steering mechanism 340 includes the second elongate member 328, a steering knob 353, and an elongate steering rod 366 disposed within a lumen 363 of the second elongate member 328 and a lumen 365 of the flexible member 362. The steering rod 366 is formed of a shape-memory material, such as nitinol or superelastic nitinol (or any other type of material that can maintain a biased configuration), and a distal end portion 368 of the steering rod 366 is heat set into a biased curved configuration as shown in FIG. 16. Thus, when the distal end portion 368 of the steering rod 366 is unconstrained, it will be biased into its curved configuration. When the distal end portion 368 of the steering rod 366 is constrained it is moved to a different curvature (e.g., substantially straight or linear). The amount of curvature of the steering rod 366 can depend on the amount or portion of the steering rod 366 that is constrained.

As shown in FIG. 13, a proximal end portion of the second elongate member 328 is received within a splined shaft of a coupler 365. A proximal end of the coupler 365 is coupled to a drive member 364, which is matingly (e.g., threadedly) coupled to the steering knob 353. To operate the steering mechanism 340, a user turns the steering knob 353 (e.g., clockwise or counter-clockwise about an axis substantially parallel to a longitudinal axis of the proximal end portion of the first elongate member 322) and the steering knob 353 causes the drive member 364 to move proximally or distally relative to the steering knob 353. Specifically, the steering knob 353 can rotate relative to the housing 342, but is held stationary in a proximal-distal position, which causes the threaded drive member 364 to move proximally or distally (depending on which direction the steering knob 353 is rotated and the direction of the grooves in steering knob 353) relative to the drive member 364. When the threaded drive member 364 moves, it in turn moves the coupler 365 in the same direction (e.g., proximally or distally). The coupler 364 then causes the second elongate member 328 to also move proximally or distally. The splined shaft of the coupler 365 allows the second elongate member 328 to translate proximally and distally while simultaneously being rotated by the drive mechanism 315.

Figure 15:
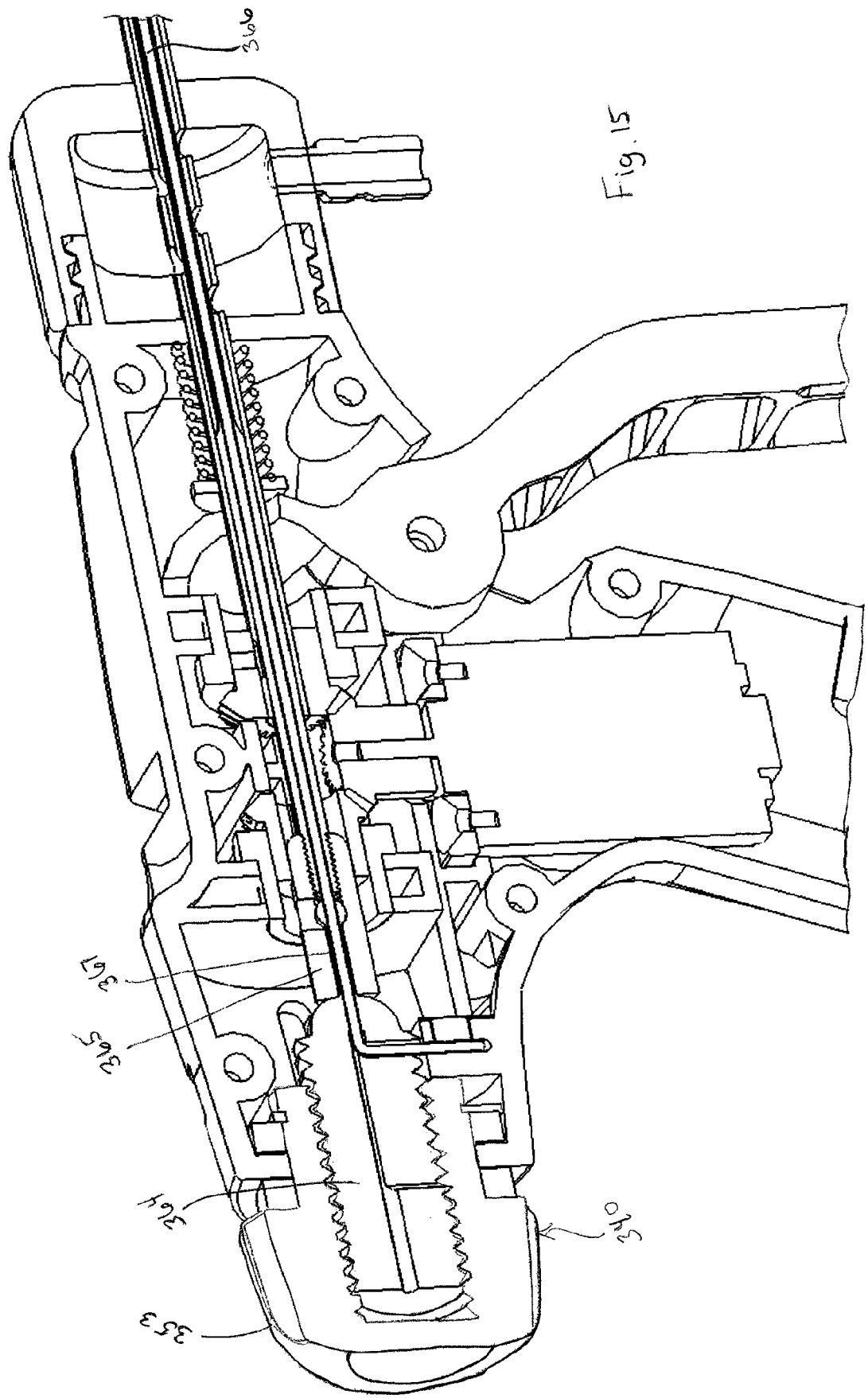
FIG. 15 is a side cross-sectional view of a portion of the medical device of FIG. 1 showing the steering mechanism in a second position.

When the second elongate member 328 (and drive member 364) is moved distally as shown in FIG. 13, the distal end portion 368 of the steering rod 366 will be disposed almost entirely within the lumen 363 of the second elongate member 328 as shown in FIG. 14. In this position, the steering rod 366 will have a first curvature (e.g., substantially linear or straight) and the flexible member 362 will also have a first curvature (e.g., substantially linear or straight configuration). When the second elongate member 328 (and drive member 364) is moved proximally, as shown in FIG. 15, the distal end portion 368 of the steering rod 366 will be at least partially disposed outside of the lumen 363 of the second elongate member 328 as shown in FIG. 16. In this position, the steering rod 366 will have a second curvature (e.g., curved configuration) as it will be allowed to assume (at least partially) its biased curved configuration. As the steering rod 366 moves to its biased curved configuration, the flexible member 362 will also be moved to a second curvature (e.g., curved configuration) based on the curvature of the steering rod 366.

An indicator rod 360 is coupled to the threaded drive member 364 and extends through a slot 374 (see FIG. 11) defined by the housing 342. The indicator 360 can be used to indicate a longitudinal position of the threaded drive member 364, and thus a relative curvature of the distal end portion of the medical device 320. For example, when the threaded drive member 364 is moved to a distal position (as shown in FIGS. 12 and 13), the indicator 360 will be in a corresponding distal position relative to the slot 374, as shown in FIGS. 11 and 12. When the threaded drive member 364 is moved to a proximal position (as shown in FIG. 15), the indicator 360 will be in a corresponding proximal position relative to the slot 374 (not shown). When the distal end portion of the medical device 320 is disposed within a patient's body, the housing 342 and indicator 360 are disposed outside the patient's body. Thus, a user can view the indicator 360 and determine an amount of relative curvature of the distal end portion of the medical device 320.

As stated above, the amount of curvature of the steering rod 366 and flexible member 362 will depend on the amount of rotation of the steering knob 353 and the corresponding distance the second elongate member 328 is moved distally over the distal end portion 368 of the steering rod 366, or moved proximally uncovering the distal end portion 368 of the steering rod 366. The steering mechanism 340 can be configured to move the second elongate member 328 proximally when the steering knob 353 is rotated clock-wise, and distally when the steering knob 353 is rotated counter-clockwise, or vice-versa.

As shown in the cross-sectional views of FIGS. 14 and 16, the flexible member 362 in this embodiment, includes a double layer of springs, and each of the two layers is coiled in an opposite direction from the other layer. Such a configuration enables the distal end portion of the medical device 320 to be maneuvered (steered or turned) in multiple directions and be returned to a linear configuration. For example, the distal end portion of the medical device 320 can be steered or turned in a first direction, and as the spring that is coiled in the first direction (referred to here as a first spring) is partially uncoiled (to allow for the turn) the second spring that is coiled in a direction opposite of the first spring applies torque in an opposite direction. This enables the flexible member 362 (i.e., the first spring) to move from a partially uncoiled configuration to a substantially linear configuration. Thus, the two springs work together to allow the flexible member 362 to be moved back and forth between curved configurations and linear configurations.

In alternative embodiments, the second elongate member can be configured to be actuated by other methods. For example, a medical device can be configured with a steering actuator that uses linear motion to cause the second elongate member to move proximally and distally, rather than rotational motion (e.g., rotation of a steering knob). For example, a lever can be coupled to the second elongate member that can be manually actuated by the user using linear motion. In other examples, a pull rod or a pulley mechanism can be used to move the second elongate member. In another example, a fly-wheel mechanism can be coupled to the second elongate member and used to move the steering tube proximally and distally. For example, the fly-wheel mechanism can have a lever arm that a user can turn or rotate to cause linear movement of the second elongate member.

The medical device 320 can be used in a variety of different medical procedures as described above for other embodiments. In one example use, the expandable member 326 can be collapsed by placing a sheath over the first elongate member 322 as described above. The sheath can be moved distally to collapse the expandable member 326. The medical device 320, with the sheath over the expandable member 326 can then be inserted through an access cannula and into a biological body. The medical device 320 can be positioned at a desired location within a biological body, such as an intervertebral disc. As the expandable member 326 emerges from a distal end of the access cannula (or from within a sheath or cannula coupled to the elongate member 322), it will assume its pre-set expanded configuration. The user can rotate the steering knob 353 to steer the distal end portion of the medical device 320 (e.g., move the flexible member 362 to a curved configuration) to a desired location within the intervertebral disc, as described above. The expandable member 326, coupled to a distal end of the flexible member 362, will in turn be moved to a desired location. As already described, the user can adjust the amount of curvature of the flexible member 362 to position the expandable member 326 at a desired location.

After the user has achieved the desired angle or position of the flexible member 362 and expandable member 326 within the intervertebral disc, the user can squeeze the lever 334 to actuate the drive mechanism 315 and cause the first elongate member 322, flexible member 362 and expandable member 326 to rotate in a first direction. The drive mechanism 315 also rotates the second elongate member 328 in a second opposite direction as described above. The arms 327 of the expandable member 326 will cut, tear, or disrupt tissue (e.g., nucleus material) within the intervertebral disc. The user can release the lever 334 to turn the drive mechanism 315 off as desired. The user can also optionally move the medical device 320 distally and proximally while the expandable member 326 is rotating. As described above for medical device 120, the rotation of the second elongate member 328 will draw tissue fragments produced by the expandable member 326 through the lumen 325 of the first elongate member 322, through the openings 354, and into the reservoir 338.

The angle or curvature of the flexible member 362 can be adjusted as desired. For example, the user can rotate the steering knob 353 to move the flexible member 362 to a substantially linear configuration or a different angle of curvature to position the expandable member 326 at a different location within the intervertebral disc. The user can steer and reposition the medical device 320 to different locations within the intervertebral disc and actuate the rotation of the expandable member 326 (and rotation of the second elongate member 328) to disrupt nucleus material at various locations within the intervertebral disc. The expandable member 326 can be rotated while the medical device 320 is being maneuvered or steered within the body, or can be rotated after the medical device 320 has been positioned at a desired location. In some cases, it may be desired to disrupt the entire nucleus material within the intervertebral disc. Various regions within the intervertebral disc can be reached without removing and reinserting the medical device 320, which can help preserve the integrity of the annulus of the intervertebral disc. Thus, continuous disruption of nucleus material can be achieved by access through a single small opening in the annulus of the disc.

After the desired amount of disruption has been completed, the flexible member 362 can be moved to a substantially linear or straight configuration and the expandable member 326 can be drawn proximally into the access cannula to collapse the expandable member 326 and remove the medical device 320 from the intervertebral disc. Irrigation and/or suction can optionally be applied to remove the disrupted nucleus material from the reservoir 338 as described above. After the disrupted material has been removed from the intervertebral disc, other procedures can be performed such as a disc replacement procedure. For example, a disc prosthesis can be implanted into the disc as disrupted material has been removed. Although the above example use of the medical device 320 referred to using a sheath to collapse the expandable member 326, in alternative embodiments, the medical device 320 (and expandable member 326) can be sized such that it can be inserted through an access cannula without collapsing the expandable member 326. In some embodiments, the medical device 320 includes a tissue interaction member that is not expandable.

FIGS. 17 and 18 illustrate a distal end portion of an embodiment of a medical device having a tissue interaction member that is not expandable. A medical device 420 includes a first elongate member 422 and a second elongate member 428 (shown in FIG. 18 only) disposed within a lumen 425 of the first elongate member 422. The first elongate member 422 and the second elongate member 428 can be rotated with a drive mechanism (not shown) as described above. The medical device 420 also includes a flexible member 462 coupled to the first elongate member 422, and a steering rod 466 disposed within a lumen 463 of the second elongate member 428 and a lumen 465 of the flexible member 462. The flexible member 462 can be similarly constructed as the flexible member 362. Thus, the medical device 420 can include a steering mechanism similar to the steering mechanism 317 described above to maneuver the medical device 420 within a body lumen in a similar manner as medical device 320.

A tissue interaction member 426 is coupled to the flexible member 462. In this embodiment, the tissue interaction member 426 includes multiple teeth 470 that can be used to cut, tear, disrupt, and/or otherwise manipulate tissue when rotated within a biological body. The tissue interaction member 426 also defines a lumen 429 through which disrupted tissue can be drawn as described above for previous embodiments. Such a tissue interaction member 426 can be incorporated in any of the embodiments of a medical device described herein.

FIGS. 19-22 illustrate an example use of an embodiment of a medical device that includes a sheath that can be manually actuated to move a tissue interaction member between a collapsed configuration and an expanded configuration. A medical device 520 can be constructed similar to the medical devices described above and can function in a similar manner. For example, the medical device 520 can include a drive mechanism (not shown in FIGS. 19-22) and/or a steering mechanism (not shown in FIGS. 19-22).

The medical device 520 includes a first elongate member 522 and an expandable tissue interaction member 526 coupled to a distal end portion of the first elongate member 522. The medical device 520 can also include a second elongate member (not shown in FIGS. 19-22) as described above. The tissue interaction member 526 has a collapsed configuration (not shown) and an expanded configuration as shown in FIGS. 20 and 22. A sheath 530 is slidably disposed over the first elongate member 528. In this embodiment, the sheath 530 can be slidably moved distally relative to the first elongate member 522 and over the tissue interaction member 526 (as shown in FIG. 19) to collapse the tissue interaction member 526. The sheath 530 can be moved proximally relative to the first elongate member 522 such that the tissue interaction member 526 is disposed outside a distal end of the sheath 530 and can assume its biased expanded configuration, as shown in FIG. 20.

FIGS. 21 and 22 illustrate the use of an optional access cannula 572 to insert the medical device 520 into a biological body. As shown in FIGS. 21 and 222 in this example use, the access cannula 572 is disposed within a nucleus N of an intervertebral disc D. The access cannula 572 can be inserted through an annulus A of the intervertebral disc D with its distal end disposed within the nucleus N of the intervertebral disc D (e.g., just inside the annular wall). The medical device 520 can then be inserted through a lumen of the access cannula 572 as shown in FIG. 21. For example, as described above the sheath 530 can be placed over the expandable member 526 to collapse the expandable member 526. The medical device 520 can then be inserted through the lumen of the access cannula 572 and into the nucleus N of the intervertebral disc D. When a distal end of the medical device 520 is in a desired position within the intervertebral disc D, the sheath 530 can be moved proximally relative to the first elongate member 522 such that the expandable member 526 is unrestrained and can move to its expanded configuration as shown in FIG. 22.

The medical device 520 can then be used to disrupt tissue (e.g., nucleus material) as described above for previous embodiments. After the desired amount of disruption has been achieved, the medical device 520 can be pulled proximally, such that the tissue interaction member 526 is pulled into the lumen of the access cannula 572 and/or within the sheath 530 and is moved to the collapsed configuration. Alternatively, the sheath 530 can be moved distally over the expandable member 526 and relative to the first elongate member 522 to collapse the tissue interaction member 526. With the tissue interaction member 526 in the expanded configuration, the medical device 520 can be removed from the disc D through the access cannula 572. The access cannula 572 can then be removed.

As described above for previous embodiments, the second elongate member (not shown) can draw disrupted tissue into a reservoir 538. In some embodiments, suction can be applied to draw the disrupted nucleus material into the reservoir and/or out of the reservoir 538 through a port (not shown).

In some embodiments, suction can be applied through the lumen of the access cannula 572. For example, after the medical device 520 is removed form the access cannula 572, a suction source (not shown) can be coupled to a proximal end of the access cannula 572 and used to provide suction within the lumen of the access cannula 572. Alternatively, a separate suction tool (not shown) can be inserted through the lumen of the access cannula 572 and used to suction nucleus material out of the intervertebral disc D and to a location outside of the patient. A saline solution can optionally be flushed through the lumen of the access cannula 572 prior to suctioning the disrupted nucleus material to mobilize the disrupted material. The optional flushing and suctioning can be repeated as necessary to remove the disrupted nucleus material.

The medical device for any of the embodiments may be constructed with any suitable material used for such a medical device. For example, the elongate members, the expandable members, and the steering rods for any embodiments can each be formed with nitinol, superelastic nitinol, or other shape-memory material. The various components of the medical device (20, 120, 320, 420, 520) can each be formed with various biocompatible metal materials, such as stainless steel, titanium, titanium alloy, surgical steel, metal alloys, or suitable biocompatible plastic materials, such as various polymers, polyetheretherketone (PEEK), carbon fiber, ultrahigh molecular weight (UHMW) polyethylene, etc., or various elastic materials, flexible materials, various rubber materials, or combinations of various materials thereof. The expandable member can also be formed with various flexible or expandable materials such as plastics (e.g., various polymers) and/or rubber materials having flexible or pliable characteristics.

Figure 23:
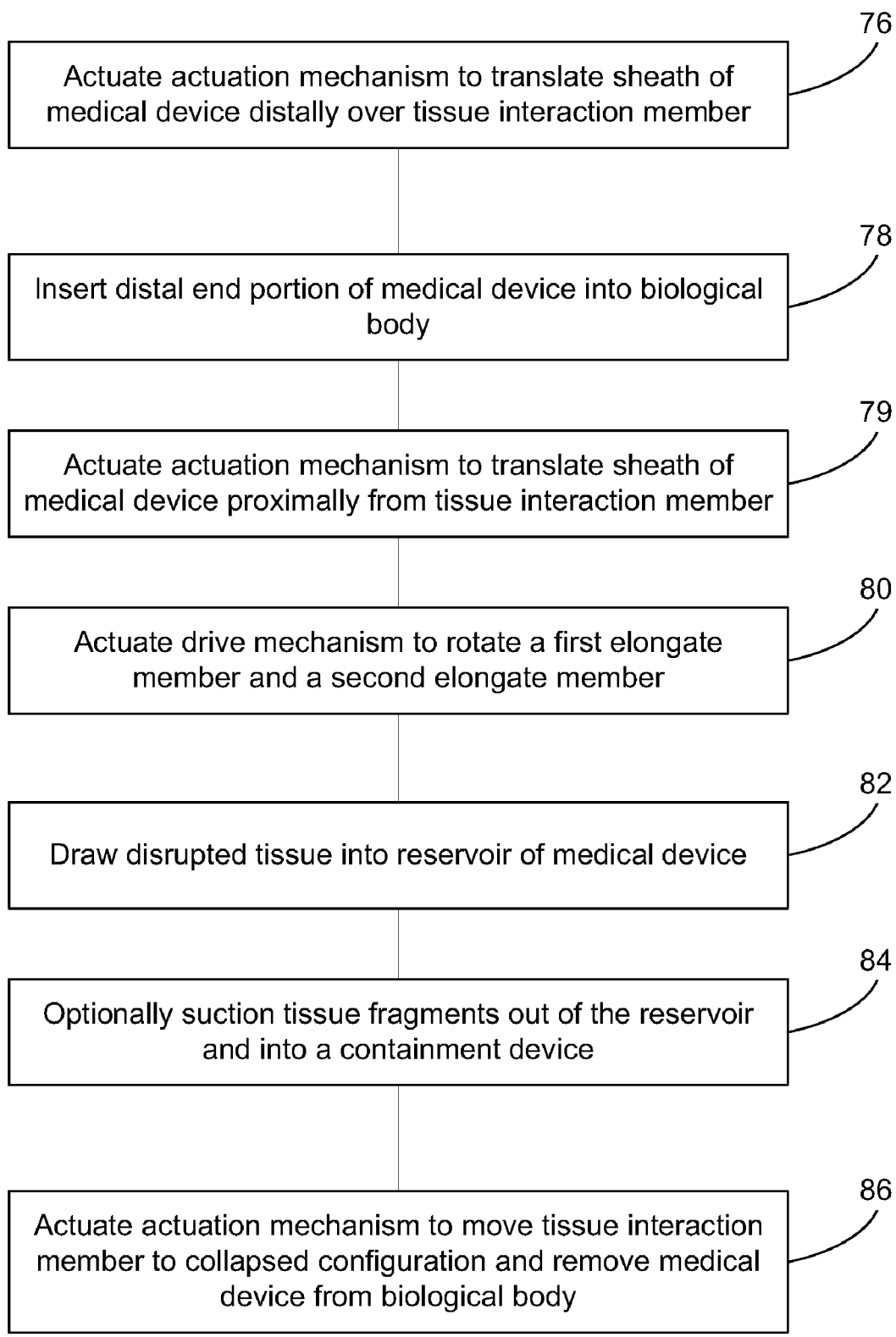
FIGS. 23 and 24 are each a flowchart of a method according to an embodiment.

FIG. 23 is a flowchart illustrating an example of a method of disrupting tissue within a biological body. The method includes at 76, actuating an actuation mechanism of a medical device (e.g., of a medical device 20, 120, 320, 420 and 520) such that a sheath of the medical device is translated distally and partially covers a tissue interaction member (e.g., an expandable member) of the medical device. This causes the tissue interaction member to at least partially collapse. The tissue interaction member can be coupled to or formed monolithically with a first elongate member of the medical device. At 78, a distal end portion (e.g., the tissue interaction member and a distal end portion of the elongate member) of the medical device is inserted into a biological body, such as a vertebra or an intervertebral disc. At 79, the actuation mechanism is actuated to translate the sheath proximally to uncover the tissue interaction member (e.g., to allow the tissue interaction member to expand or deploy). At 80, a drive mechanism is actuated (e.g., turned from off to on) to cause automated rotation of the first elongate member and automated rotation of a second elongate member of the medical device movably disposed within a lumen of the first elongate member as described herein. In some embodiments, the rotation of the first elongate member is rotated in an opposite direction as the second elongate member. As the elongate members are rotated, tissue within the biological body is disrupted by the tissue interaction member.

At 82, disrupted tissue is drawn into a reservoir of the medical device. For example, the second elongate member is configured to draw tissue fragments through a lumen of the first elongate member and into the reservoir. At 84, an optional suction source is coupled to the reservoir and can be actuated to suction tissue fragments out of the reservoir and into a containment device. For example, a suction source can be coupled to a port of the reservoir via a suction line, hose or conduit. At 86, the actuation mechanism can be actuated to move the tissue interaction member to a collapsed configuration and remove the medical device from the biological body.

Figure 24:
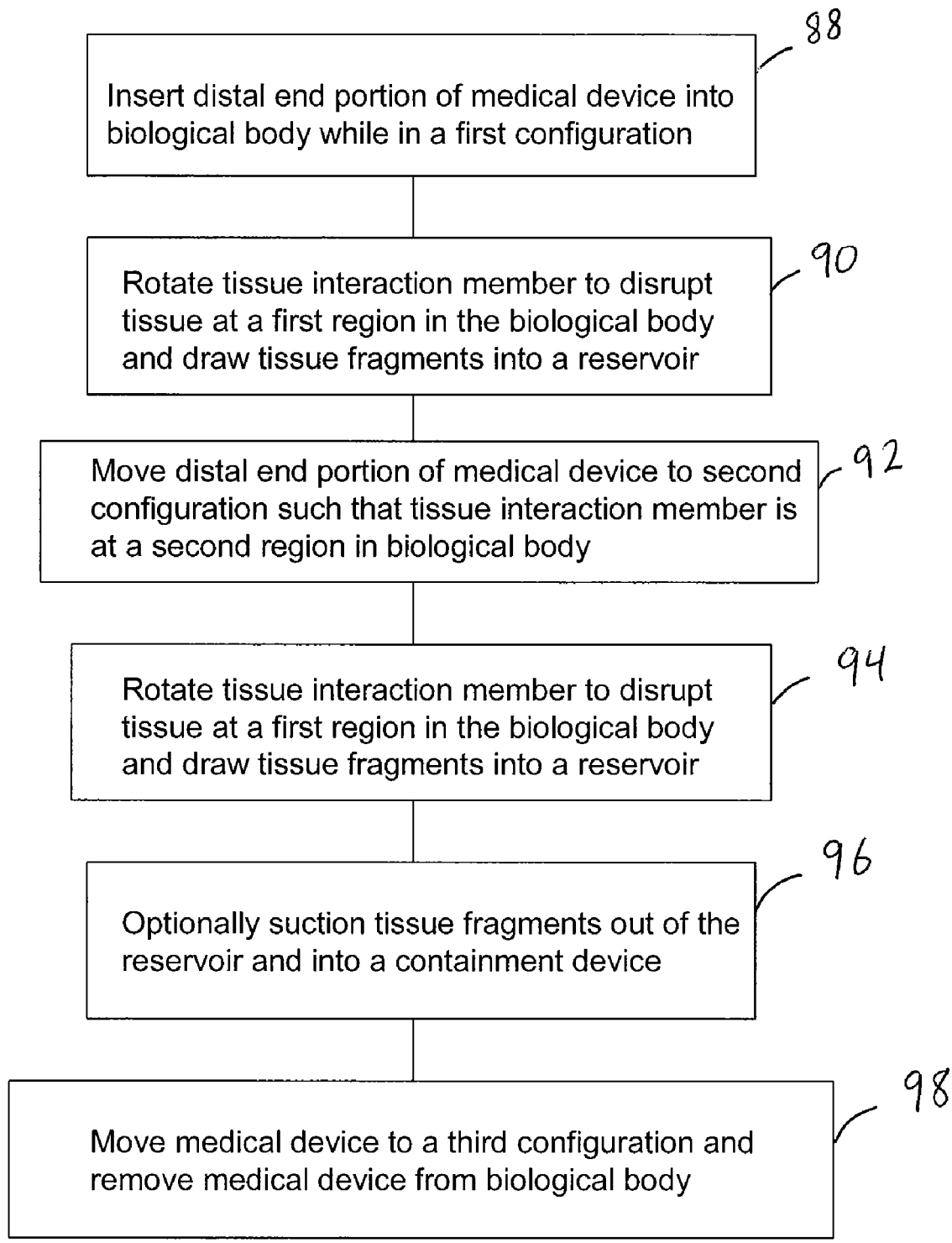

FIG. 24 is a flowchart illustrating another method of disrupting tissue within a biological body. The method includes at 88, inserting a distal end portion of a medical device into a biological body while the distal end portion of the medical device is in a first configuration (e.g., a substantially linear configuration). The biological body can be for example, a vertebra or an intervertebral disc. The medical device includes a tissue interaction member disposed at a distal end of the medical device. The tissue interaction member is disposed at a first region within the biological body after being inserted. At 90, the tissue interaction member is rotated such that tissue is disrupted within the biological body at the first region and tissue fragments are drawn into a reservoir of the medical device.

At 92, the distal end portion of the medical device is moved to a second configuration (e.g., a curved configuration) while disposed within the biological body such that the tissue interaction member is disposed at a second region within the biological body different from the first region. At 94, the tissue interaction member is rotated such that tissue is disrupted at the second region and tissue is drawn into the reservoir of the medical device. At 96, an optional suction source is coupled to the reservoir and can be actuated to suction tissue fragments out of the reservoir and into a containment device. At 98, the distal end portion of the medical device is moved to a third configuration (e.g., a substantially linear configuration) and then the medical device is removed from the biological body. Note that the third configuration may be the same as or differ from the first configuration.

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although various embodiments have been described as having particular features and/or combinations of components, other embodiments are possible having any combination or sub-combination of any features and/or components from any of the embodiments described herein. For example, although the steering mechanism was described with reference to medical device 320, a steering mechanism can be incorporated in any of the embodiments of a medical device. In addition, a manually translated sheath, such as a sheath 530 shown in FIGS. 19-22, can be included in any embodiment of a medical device, or a translating sheath coupled to the actuation mechanism as described with reference to medical device 120 can be included in any embodiment.

Further, the various components of a medical device as described herein can have a variety of different shapes and or size not specifically illustrated. For example, the tissue interaction members (e.g., expandable members) can include various quantities of arms, and/or can be a variety of different shapes or sizes. The elongate members can be various lengths and have various cross-sections. The elongate members can have a lumen or can be solid depending on its particular function.

Also, the drive mechanism, gear mechanism and/or steering mechanism can be used to actuate and/or maneuver other types of tissue interaction members not specifically described. For example, although the medical devices described herein included an expandable tissue interaction member (e.g., 126, 226, 326, 526), or a non-expandable tissue interaction member, such as tissue interaction member 426, disposed at a distal end thereof, other types of tissue interaction members can alternatively be incorporated in a medical device as described herein. For example, other types and configurations of scraping, cutting, curetting, disrupting, or debulking tools can be used. In addition, the use of a sheath or cannula, such as cannula 130 or sheath 530, may not be needed depending on the particular configuration of the tissue interaction member. For example, a cannula or sheath may not be needed to collapse a tissue interaction member that does not have an expanded configuration. In addition, other types of mechanisms used to expand or collapsed a tissue interaction member can be alternatively used. For example, a medical device may include a pull rod configured to move a tissue interaction member between a collapsed configuration and an expanded configuration.

Various features and/or components of the medical devices described herein can be used in a device that can be manually actuated such as the medical devices described in U.S. patent application Ser. No. 12/109,565, filed Apr. 25, 2008, entitled, "Medical Device With One-Way Rotary Drive Mechanism" ("the '565 application"), the disclosure of which is incorporated herein by reference in its entirety. Further, various features and/or components described in the '565 application can be included in a medical device described herein.

Although the use of a medical device was described with a specific example of use within an intervertebral disc, it should be understood that the medical device and methods described herein can be used in other areas of a patient. For example, the medical device can be used in other areas within a spine, such as within a vertebra, as well as other bone or soft tissue areas within a patient's body.

In addition, the tissue interaction members (e.g., 126, 226, 326, 426, 526) can alternatively be coupled to other types of medical devices and used to cut, tear, debulk, or otherwise disrupt tissue as described above. The tissue interaction members can also be used independently in that they can each be used without providing a mechanism to rotate the elongate member for which the tissue interaction member is attached or formed therewith. For example, as described above, an expandable tissue interaction member can be inserted into a biological body and actuated between an expanded configuration and a collapsed configuration such that tissue is captured within the tissue interaction member. In another example, a tissue interaction member can be manually rotated and/or translated within a biological body to disrupt tissue.

What is claimed is:

1. An apparatus, comprising:
a first elongate member defining a lumen;
a second elongate member movably disposed within the lumen of the first elongate member, the second elongate member having a threaded exterior surface and defining a lumen, the threaded exterior surface including helical threads having a direction associated with a direction of rotation of the second elongate member; and
a third elongate member movably disposable within the lumen of the second elongate member, the third elongate member movable between a first configuration in which a distal end portion of the first elongate member has a first curvature and a second configuration in which the distal end portion of the first elongate member has a second curvature different than the first curvature, the first elongate member, the second elongate member and the third elongate member collectively configured to be inserted into a biological body when the third elongate member is in the first configuration, the distal end portion of the first elongate member being movable to the second curvature while disposed within the biological body.

2. The apparatus of claim 1, further comprising: a reservoir coupled to the first elongate member, the lumen of the first elongate member in fluid communication with the reservoir, the second elongate member configured to draw tissue through the lumen of the first elongate member and into the reservoir when the second elongate member is rotated relative to the first elongate member.

3. The apparatus of claim 1, further comprising:
a handle, the drive motor being at least partially disposed within the handle;
a lever coupled to the handle;
a sheath coupled to the lever and extending around the elongate member, the sheath defining a lumen, the sheath configured to translate along a centerline of a distal end portion of the first elongate member upon actuation of the lever from a first position in which the tissue interaction portion is entirely disposed within the lumen of the sheath and a second position in which the tissue interaction portion is entirely disposed outside of a distal end of the sheath.

4. The apparatus of claim 1, further comprising:
a first bevel gear coupled to the first elongate member; and
a second bevel gear coupled to the second elongate member, the drive motor configured to engage the first bevel gear and the second bevel gear to rotate the first elongate member and the second elongate member substantially simultaneously.

5. The apparatus of claim 1, further comprising: a handle, the drive motor being at least partially disposed within the handle; and a battery holder disposed within the handle and coupled to the drive motor.

6. The apparatus of claim 1, further comprising: a sheath defining a lumen, the first elongate member being at least partially disposed within the lumen of the sheath, the first elongate member defining an opening in a side wall of the first elongate member and in fluid communication with the lumen of the sheath; and a reservoir coupled to the sheath, the sheath defining an opening in a side wall of the sheath and in fluid communication with the reservoir, the threaded portion of the second elongate member including helical threads having a direction associated with the direction of rotation of the second elongate member, the second elongate member configured to draw tissue through the lumen of the first elongate member and into the reservoir when the second elongate member is rotated.

7. The apparatus of claim 1, further comprising: a sheath, the first elongate member at least partially disposed within a lumen of the sheath, the sheath configured to translate between a first position in which the tissue interaction member is disposed at least partially within a lumen defined by the sheath and a second position in which the tissue interaction member is entirely disposed outside of a distal end of the sheath.

8. The apparatus of claim 1, wherein the tissue interaction member includes a plurality of deformable arms, each arm from the plurality of deformable arms having a serrated edge configured to disrupt tissue within the biological body.

9. The apparatus of claim 1, further comprising: a flexible member disposed at a distal end portion of the first elongate member; and a third elongate member movably disposed within a lumen defined by the second elongate member, the third elongate member movable between a constrained configuration in which the flexible member has a first curvature and an unconstrained configuration in which the flexible member has a second curvature different than the first curvature.

10. The apparatus of claim 1, further comprising:
a drive motor at least partially disposed within the handle;
a first bevel gear coupled to the first elongate member; and
a second bevel gear coupled to the second elongate member, the drive motor configured to engage the first bevel gear and the second bevel gear to rotate the first elongate member and the second elongate member substantially simultaneously.

11. The apparatus of claim 1, further comprising: a tissue interaction member disposed at a distal end of the first elongate member, the tissue interaction member configured to disrupt tissue within the biological body.

12. The apparatus of claim 11, wherein the tissue interaction portion has a collapsed configuration and an expanded configuration, the tissue interaction portion configured to disrupt tissue within the biological body when in the expanded configuration, wherein the tissue interaction portion includes a plurality of arms and in the expanded configuration each of the arms includes a flared and spiral configuration and serrations along a length of a leading edge.

13. The apparatus of claim 11, further comprising:
a drive motor at least partially disposed in the handle and coupled to the first elongate member and coupled to the second elongate member, the drive motor configured to rotate the first elongate member in a first direction and configured to rotate the second elongate member in a second direction opposite the first direction;
a lever coupled to the handle; and
a sheath coupled to the lever and extending around a first elongate member, the sheath defining a lumen, the sheath configured to translate along a centerline of a distal end portion of the first elongate member upon actuation of the lever from a first position in which the tissue interaction portion is entirely disposed within the lumen of the sheath and a second position in which the tissue interaction portion is entirely disposed outside of a distal end of the sheath.

14. The apparatus of claim 11, wherein the tissue interaction member has a collapsed configuration and an expanded configuration, the tissue interaction member configured to disrupt tissue within the biological body when in the expanded configuration, wherein the tissue interaction portion includes a plurality of arms and in the expanded configuration each of the arms includes a flared and spiral configuration and serrations along a length of a leading edge of the arm.

15. The apparatus of claim 1, further comprising: a drive motor coupled to the first elongate member and coupled to the second elongate member, the drive motor configured to rotate the first elongate member in a first direction and configured to rotate the second elongate member relative to the first elongate member in a second direction opposite the first direction.

16. The apparatus of claim 1, wherein a distal end portion of the first elongate member includes a plurality of elastically deformable arms configured to disrupt tissue within the biological body, the plurality of elastically deformable arms collectively having an unconstrained expanded configuration, each deformable arm form the plurality of deformable arms having a serrated edge portion.

17. The apparatus of claim 1, wherein the third elongate member is in the second configuration when at least a portion of the third elongate member is disposed outside the lumen of the second elongate member.

18. The apparatus of claim 1, wherein the distal end portion of the first elongate member includes a flexible portion, the tissue interaction member being coupled to a distal end of the flexible portion, the flexible portion being movable between the first configuration and the second configuration.

* * * * *